United States Patent
Aubert et al.

(10) Patent No.: US 10,292,921 B2
(45) Date of Patent: *May 21, 2019

(54) HAIR DYEING PROCESS USING A COMPOSITION COMPRISING AT LEAST ONE INDOL(IN)E COMPOUND AND A POLYCYCLIC AROMATIC COMPOUND CONTAINING AT LEAST TEN CARBON ATOMS

(71) Applicant: L'OREAL, Paris (FR)

(72) Inventors: Fabien Aubert, Paris (FR); Arno Wahler, Maisons Laffite (FR); Marie Mignon, Paris (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/313,716

(22) PCT Filed: May 27, 2015

(86) PCT No.: PCT/EP2015/061735
§ 371 (c)(1),
(2) Date: Nov. 23, 2016

(87) PCT Pub. No.: WO2015/181244
PCT Pub. Date: Dec. 3, 2015

(65) Prior Publication Data
US 2018/0092822 A1    Apr. 5, 2018

(30) Foreign Application Priority Data

May 27, 2014 (FR) .................................... 14 54757

(51) Int. Cl.
| | | |
|---|---|---|
| *A61Q 5/10* | (2006.01) | |
| *A61K 8/49* | (2006.01) | |
| *A61K 8/34* | (2006.01) | |
| *A61K 8/22* | (2006.01) | |
| *A61K 8/41* | (2006.01) | |

(52) U.S. Cl.
CPC ............... *A61K 8/492* (2013.01); *A61K 8/22* (2013.01); *A61K 8/347* (2013.01); *A61K 8/411* (2013.01); *A61K 8/49* (2013.01); *A61K 8/4906* (2013.01); *A61Q 5/10* (2013.01); *A61K 2800/884* (2013.01)

(58) Field of Classification Search
CPC . A61K 8/19; A61K 8/22; A61K 8/492; A61K 8/27; A61K 2800/4324; A61Q 5/10
See application file for complete search history.

(56) References Cited

U.S. PATENT DOCUMENTS

| | | | |
|---|---|---|---|
| 3,376,110 A | 4/1968 | Shiraeff | |
| 4,823,985 A | 4/1989 | Grollier et al. | |
| 5,008,093 A | 4/1991 | Merianos | |
| 5,183,901 A | 2/1993 | Login et al. | |
| 5,690,697 A | 11/1997 | Samain | |
| 6,540,793 B1 * | 4/2003 | Lim ........................ | A61K 8/411 |
| | | | 549/358 |
| 8,597,373 B2 * | 12/2013 | Guerin ..................... | A61K 8/19 |
| | | | 8/405 |
| 2002/0032938 A1 | 3/2002 | Matzik et al. | |
| 2003/0103917 A1 | 6/2003 | Pruche | |
| 2003/0163878 A1 | 9/2003 | Pruche | |
| 2003/0208857 A1 | 11/2003 | Matzik et al. | |
| 2013/0174864 A1 | 7/2013 | Guerin et al. | |

FOREIGN PATENT DOCUMENTS

| | | | |
|---|---|---|---|
| DE | 10057532 A1 | 5/2002 | |
| DE | 102005062830 A1 | 1/2007 | |
| EP | 0697209 A1 | 2/1996 | |
| EP | 1433470 A1 | 6/2004 | |
| EP | 1707242 A1 | 10/2006 | |
| FR | 2586913 A1 | 3/1987 | |
| FR | 2814943 A1 | 4/2002 | |
| FR | 2814945 A1 | 4/2002 | |
| FR | 2814946 A1 | 4/2002 | |
| FR | 2814947 A1 | 4/2002 | |
| FR | 2961393 A1 | 12/2011 | |
| WO | 93/09759 A1 | 5/1993 | |
| WO | 2008/151858 A2 | 12/2008 | |
| WO | WO 2011/157668 A1 * | 12/2011 | ............... A61Q 5/10 |

OTHER PUBLICATIONS

International Search Report for PCT/EP2015/061735, dated Jul. 30, 2015.

* cited by examiner

*Primary Examiner* — Eisa B Elhilo
(74) *Attorney, Agent, or Firm* — The Marbury Law Group, PLLC

(57) ABSTRACT

The invention relates to a process for dyeing keratin fibers by treating said fibers with i) at least one aromatic compound comprising a hydrocarbon-based polycycle comprising at least 10 carbon atoms, at least one of the rings of which is aromatic, ii) at least one indol(in)e compound; optionally iii) at least one metal salt, iv) at least hydrogen peroxide or at least one hydrogen peroxide-generating system and v) at least one basifying agent; to a dye composition comprising ingredients i) and ii), and optionally iii) to v) as defined previously and to a kit comprising ingredients i) to v) as defined previously. This hair dyeing process makes it possible to obtain better colorings which are more uniform, chromatic and long-lasting and which do not impair the cosmetic properties of the keratin fibers, and prevents changing of the color associated with the presence of indol(in)e derivatives.

24 Claims, No Drawings

HAIR DYEING PROCESS USING A COMPOSITION COMPRISING AT LEAST ONE INDOL(IN)E COMPOUND AND A POLYCYCLIC AROMATIC COMPOUND CONTAINING AT LEAST TEN CARBON ATOMS

CROSS REFERENCE TO RELATED APPLICATIONS

This is a national stage application of PCT/EP2015/061735, filed internationally on May 27, 2015, which claims priority to French Application No. 1454757, filed on May 27, 2014, both of which are incorporated by reference herein in their entireties.

The invention relates to a process for dyeing keratin fibres by treating said fibres with i) at least one aromatic compound comprising a hydrocarbon-based polycycle comprising at least 10 carbon atoms, at least one of the rings of which is aromatic, ii) at least one indol(in)e compound; iii) at least one metal salt, iv) optionally at least hydrogen peroxide or at least one hydrogen peroxide-generating system and v) optionally at least one basifying agent; to a dye composition comprising ingredients i) and ii), and optionally iii) to v) as defined previously and to a multi-compartment kit comprising ingredients i) to v) as defined previously.

It is known practice to obtain "permanent" colourings with dye compositions comprising oxidation dye precursors, generally known as oxidation bases, such as ortho- or para-phenylenediamines, ortho- or para-aminophenols and heterocyclic compounds. These oxidation bases are colourless or weakly coloured compounds, which, when combined with oxidizing products, may give rise to coloured compounds via a process of oxidative condensation. It is also known that the shades obtained may be varied by combining these oxidation bases with couplers or colouring modifiers, the latter being chosen especially from aromatic meta-diamines, meta-aminophenols, meta-diphenols and certain heterocyclic compounds such as indole compounds. This oxidation dyeing process consists in applying to the keratin fibres bases or a mixture of bases and couplers with hydrogen peroxide ($H_2O_2$ or aqueous hydrogen peroxide solution), as oxidizing agent, in leaving it to diffuse, and then in rinsing the fibres. The colourings resulting therefrom are permanent, strong and resistant to external agents, especially to light, bad weather, washing, perspiration and rubbing.

However, the commercial hair dyes which contain them may have drawbacks, such as problems of staining, odour, comfort and damage to keratin fibres. This is particularly the case with oxidation dyeing operations.

In the field of dyeing, it is also known practice to dye keratin materials, such as the hair or the skin, using ortho-diphenol compounds in the presence of a metal salt, in particular an Mn and/or Zn salt. In particular, patent applications FR 2 814 943, FR 2 814 945, FR 2 814 946 and FR 2 814 947 propose compositions for dyeing the skin or keratin fibres, comprising a dye precursor that contains at least one ortho-diphenol, Mn and/or Zn oxides and salts, alkaline agents of hydrogen carbonate type in a particular Mn, Zn/hydrogen carbonate ratio and optionally an enzyme. According to these documents, it is possible to obtain intense colourings while dispensing with the use of hydrogen peroxide. However, the colourings obtained are not strong enough, in particular in the case of hair fibres.

It is also known practice to dye keratin fibres with indole or indoline derivatives in the presence of a metal salt, especially of Mn. Patent application EP 697 209 in particular describes a two-step dyeing process using, in a first step, an indole or indoline dye in the presence of a manganese salt, and, in a second step, a basifying agent optionally combined with an oxidizing agent. However, the results obtained via that process are not entirely satisfactory in terms of intensity of colouring, and the risks of bleaching and of attack of the keratin fibres are non-negligible.

Moreover, the problem of changing of the colour is a real problem of hair colouring resulting from self-oxidizing dyes. Specifically, when a hair colouring composition or dye composition comprising indol(in)e compounds substituted especially with one or two hydroxyl groups such as 5,6-dihydroxyindole or 5,6-dihydroxyindoline is applied to keratin fibres, the colouring obtained may change after several days, especially with a change in shade (changing of the colour) and in particular may undergo yellowing over time. On the other hand the colour uptake obtained with indol(in)e compounds is not always satisfactory.

This(these) technical problem(s) has(have) been solved by the present invention, one subject of which is a process for dyeing keratin fibres, in which said fibres are treated:
with a composition (A) comprising:
  i) one or more indole or indoline compounds;
  ii) one or more aromatic compounds comprising a hydrocarbon-based polycycle comprising at least 10 carbon atoms, at least one of the rings of which is aromatic, especially selected from (di)hydroxynaphtalene compounds such as 2,7-dihydroxynaphtalene;
  iii) optionally one or more metal salts;
  iv) optionally hydrogen peroxide or one or more hydrogen peroxide-generating systems; and then
optionally with a composition (B) comprising:
  v) one or more basifying agents.

Another subject of the invention relates to a composition comprising ingredients i) to v) as defined previously and to a multi-compartment device comprising ingredients i) to v) as defined previously.

Another subject of the invention is the use of one or more ingredients ii) as defined previously, for the purpose of stabilizing the colour or preventing changing of the colour arising during the ageing of the self-coupling products of the compounds i), especially for preventing yellowing.

The process according to the invention has the advantage of giving on human keratin fibres powerful, intense, chromatic colourings that are resistant to washing, perspiration, sebum and light and that are thus long-lasting and furthermore without impairing said fibres. Moreover the color uptake obtained with the process according to the invention is high. Furthermore, the colourings obtained using the process give uniform colours from the root to the end (tip) of a fibre (little colouring selectivity).

In particular, it appears that the presence of aromatic compound(s) comprising a hydrocarbon-based polycycle comprising at least 10 carbon atoms, at least one of the rings of which is aromatic such as (di)hydroxynaphthalenes, makes it possible to prevent changing of the shade (or changing of the colour) of keratin fibres dyed with indole or indoline compounds i) as defined previously, even after several days especially exposed to light.

i) Indole or Indoline Compound(s)

The indole or indoline compound(s) i) as mentioned previously, also written as "indol(in)e(s)", used in the invention are preferentially of formula (I) below:

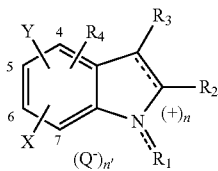

(I)

and also the organic or mineral acid or base salts thereof, optical isomers thereof: enantiomers and diastereoisomers, geometrical isomers and tautomers thereof, and solvates thereof such as hydrates;

in which formula (I):

$R_1$ represents a hydrogen atom, a $(C_1-C_6)$alkyl, $(C_2-C_6)$alkenyl, $(C_1-C_6)$alkylcarbonyl, $(C_2-C_6)$alkenylcarbonyl, $(C_1-C_6)$alkylthiocarbonyl, $(C_2-C_6)$alkenylthiocarbonyl radical or a radical $R_g$—O—S(O)$_x$— with $R_g$ representing a hydrogen atom, an alkali metal or alkaline-earth metal, or a $(C_1-C_4)$alkyl and x being equal to 1 or 2, said alkyl or alkenyl groups being optionally substituted, particularly with a heterocyclic group such as heterocycloalkenyl, and said heterocycle being optionally substituted with one or more groups such as carboxyl; preferentially, $R_1$ represents a hydrogen atom, a $(C_1-C_4)$alkyl radical such as methyl or ethyl or the following group:

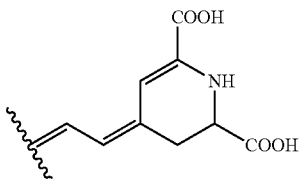 [SMILES: *=C/C=C1\C=C(C(=O)O)NC(C(=O)O)C1]

with n being 1 and ⁓ representing the point of attachment of the radical to the ammonium N⁺ of the indolium or of the indolinium (I);

$R_2$ represents a hydrogen atom, a $(C_1-C_6)$alkyl radical, or —C(Z)—Z'—$R_a$ such as —C(O)OH or —COO⁻; with $R_a$ representing a hydrogen atom, an alkali metal or alkaline-earth metal, or a $(C_1-C_6)$alkyl radical; Z and Z', which may be identical or different, represent an oxygen or sulfur atom, a group $NR_b$ or $N^+R_bR_c$, Q''; Z' may also represent a covalent σ bond with $R_a$, $R_b$ and $R_c$, which may be identical or different, representing a hydrogen atom or a $(C_1-C_6)$alkyl radical and Q'⁻ represents an anionic counterion;

$R_3$ represents i) a hydrogen atom; ii) a $(C_1-C_6)$alkyl radical optionally substituted especially with a group —$NR_bR_c$, $N^+R_aR_bR_c$, Q'⁻ or —C(Z)—Z'—$R_a$ with Z, Z', $R_a$, $R_b$, $R_c$ and Q'⁻ being as defined previously; iii) a radical (II)

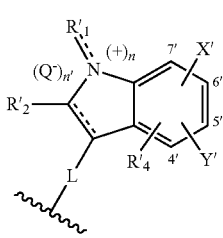

(II)

in which radical (II):

L represents a covalent σ bond, or a divalent group chosen from —Z— and —C(Z)Z'— or a divalent group $(C_1-C_6)$alkylene with Z and Z' as defined previously; particularly, L represents a σ bond, $R'_1$, $R'_2$ and $R'_4$ represent the same atoms or radicals as $R_1$, $R_2$ and $R_4$, respectively;

⁓ represents the point of attachment of the radical (II) to the rest of the molecule;

preferentially, $R_3$ represents a hydrogen atom, a $(C_1-C_4)$alkyl radical such as methyl or ethyl; an alkylamine radical;

or alternatively $R_1$ and $R_2$ and/or $R_2$ and $R_3$ form, together with the atoms that bear them, a fused, optionally substituted heterocyclic group; or $R_2$ and $R_3$ form, together with the carbon atoms that bear them, a fused, optionally substituted aryl group such as: a) benzo optionally substituted especially with groups $(C_1-C_4)$alkyl, —OH or —C(Z)Z'$R_a$ such as —C(O)H; or b) pyrido optionally substituted with a $(C_1-C_4)$alkyl group;

$R_4$ represents: i) a hydrogen atom; ii) a halogen atom such as chlorine; iii) a group —NRR' such as —NH$_2$; iv) an —OH group; v) a $(C_1-C_6)$alkyl radical; vi) a $(C_1-C_6)$ alkoxy radical; vii) a $(C_1-C_6)$alkylthio radical; viii) an aryloxy radical; viii) an arylthio radical; ix) an aryl($C_1$-$C_6$)alkoxy radical such as benzoxy; x) an aryl($C_1$-$C_6$)alkylthio radical and xi) a radical $R_aC(Z_a)$—$Z_b$— with $Z_a$ and $Z_b$ representing an oxygen or sulfur atom or $NR_b$, $R_a$ and $R_b$ being as defined previously; xii) a radical (III):

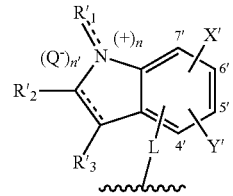

(III)

in which radical (III):

L is as defined previously, particularly L represents a σ bond, more particularly L is in position 4', $R'_1$, $R'_2$ and $R'_3$ represent the same atoms or radicals as $R_1$, $R_2$ and $R_3$, respectively;

⁓ represents the point of attachment of the radical (III) to the rest of the molecule;

particularly, $R_4$ represents a hydrogen atom;

X and X', which may be identical or different, denote a hydrogen atom or a radical chosen from —NRR' such as —NH$_2$, —OR$_e$, —SR$_e$, $(C_1-C_6)$alkyl, and $R_aC(Z_a)$—$Z_b$— as defined previously and $R_e$ representing a hydrogen atom or a group $(C_1-C_6)$alkyl, aryl, aryl($C_1$-$C_6$)alkyl such as benzyl; X and X' preferentially representing a radical —OH or a radical $(C_1-C_4)$alkyl such as methyl;

Y and Y', which may be identical or different, denote a group chosen from —OR'$_e$, —SR'$_e$, —NRR' such as —NH$_2$, $R_aC(Z_a)$—$Z_b$— as defined previously, $R_f$—O—S(O)$_x$—$Z_d$— and $R_f$—O—S(O)$_x$— with $R_f$ representing a hydrogen atom, an alkali metal or alkaline-earth metal, or a $(C_1-C_4)$alkyl, $Z_d$ representing an oxygen atom or a group NR with R as defined previously, x as defined previously and $R'_e$ representing the same atoms or radicals as $R_e$; or alternatively the radicals $R_e$ and $R_{e'}$ of two contiguous groups X and X' and/or contiguous groups Y and Y' form, together with the oxygen or sulfur atom, a heterocyclic group;

the radicals X, Y, X' and Y' being located on any of the carbon atoms 4 to 7 and 4' to 7', respectively; particularly X and Y are in position 5 and 6; X' and Y' are in position 5' and 6' and preferentially X and Y; X' and Y' represent a hydroxyl group or $R_aC(O)$—O— such as acyl-O—;

R and R', which may be identical or different, represent a hydrogen atom or an optionally substituted group $(C_1-C_6)$alkyl, such as $(C_1-C_4)$alkyl; preferentially, R and R' represent a hydrogen atom;

---- represents a single bond or a double bond;

n is 0 when the bond between $R_1$ and N or $R'_1$ and N is a single bond;

n is 1 when the group $R_1$ or $R'_1$ represents an alkenyl group and when the end linked to the nitrogen atom is a double bond, preferentially, said double bond is conjugated;

$Q^-$ represents an anionic counterion;

n' is 0 or 1;

it being understood that:

$R_3$ cannot represent the radical (II) when $R_4$ represents the radical (III); and when n is 0, then n' is 0, when n is 1, then n' is 1, or n' is 0, in which case a radical —C(Z)Z'—$R_a$ is in the anionic form —C(Z)—Z'$^-$.

According to a particular embodiment of the invention, the compounds of formula (I) are monomers, i.e. $R_3$ represents i) a hydrogen atom; or ii) an optionally substituted radical $(C_1-C_6)$alkyl.

According to another preferred embodiment of the invention, the compound(s) of formula (I) are dimers, i.e. $R_3$ represents a radical (II) or $R_4$ represents a radical (III). More particularly, the compound(s) of formula (I) are symmetrical dimers, i.e. they have a $C_2$ axis of symmetry, such as the compound 3,3'-bi-1H-indole-5,5',6,6'-tetrol (40) defined below.

According to one advantageous embodiment of the invention, the compounds of formula (I) are indole compounds with the bond ---- between the carbon atoms bearing the radicals $R_2$ and $R_3$ representing a double bond. More particularly, the indole compounds are such that X and/or Y, X' and/or Y' represent a hydroxyl group, $(C_1-C_6)$alkoxy $(C_1-C_6)$alkylcarbonyloxy preferably hydroxyl group.

Preferentially, the indole compounds that may be used in the dye composition (A) defined above may correspond to formula (Ia) below:

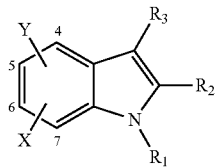

(Ia)

in which formula (Ia):

$R_1$ and $R_3$, which may be identical or different, represent a hydrogen atom or a $C_1-C_4$ alkyl radical, preferably hydrogen;

$R_2$ represents a hydrogen atom or a $C_1-C_4$ or —C(O)—OH radical, preferably hydrogen;

X denotes a hydrogen atom, —NH$_2$, —OH, a $C_1-C_4$ alkyl radical, a $C_1-C_4$ alkoxy radical or a radical —O—C(O)—R with R representing H or $C_1-C_4$ alkyl such as methyl;

Y denotes —OH, —NH$_2$ or a radical —O—C(O)R with R as defined previously; particularly —OH, — or a radical —O—C(O)R with R as defined previously, and more particularly —OH; preferably, Y is in position 6 and X is in position 7 or 5, preferably Y is in position 6 and X is in position 5; and also the organic or mineral acid or base salts thereof.

As indole compounds of formula (I) or (Ia) according to the invention, mention may be made of 5,6-dihydroxyindole, 2-methyl-5,6-dihydroxyindole, 3-methyl-5,6-dihydroxyindole, 4-hydroxyindole, 2,3-dimethyl-5,6-dihydroxyindole, 6-hydroxy 5-methoxyindole, 6-hydroxyindole, 5-hydroxyindole, 7-hydroxyindole, 7-aminoindole, 5-aminoindole, 5,6-dihydroxyindole-2-carboxylic acid, 5-aminoindole, 1-methyl-5,6-dihydroxyindole, 5-acetyloxy-6-hydroxyindole, 6-acetyl-5-hydroxyindole and 5,6-diacetyloxyindole, and the organic or mineral acid or base salts thereof.

According to another variant of the invention, the indole compounds are chosen from the following compounds:

5,6-dihydroxyindole

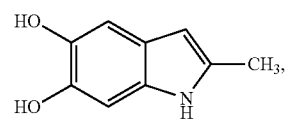

2-methyl-5,6-dihydroxyindole

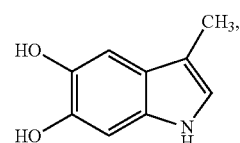

3-methyl-5,6-dihydroxyindole

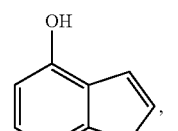

4-dihydroxyindole

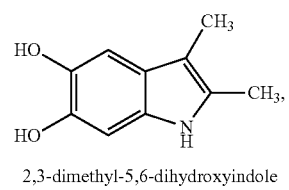

2,3-dimethyl-5,6-dihydroxyindole

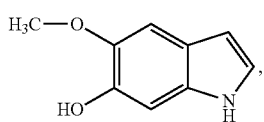
6-hydroxy-5-methoxyindole (6)

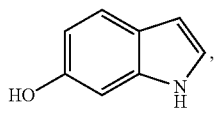
6-hydroxyindole (7)

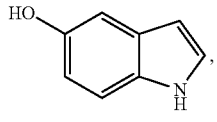
5-hydroxyindole (8)

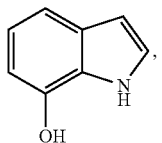
7-hydroxyindole (9)

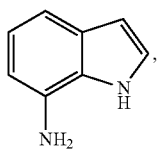
7-aminoindole (10)

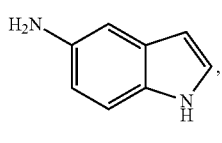
5-aminoindole (11)

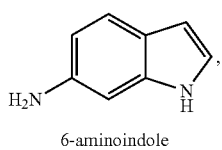
6-aminoindole (12)

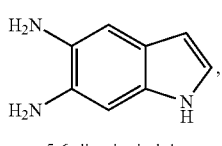
5,6-diaminoindole (13)

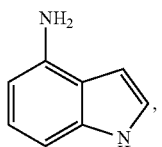
4-aminoindole (14)

5,6-dihydroxyindole-2-carboxylic acid, or 5,6-dihydroxy-1H-indole-2-carboxylic acid (15)

5-acetyloxy-6-hydroxyindole (16)

5,6-dimethylcarbonyloxy-1-methyl-1H-indole (17)

6-acetyloxy-5-hydroxyindole (18)

5,6-diacetyloxyindole (19)

5,6-dihydroxy-1-methyl-1H-indole or 1-methyl-5,6-dihydroxyindole (20)

6-hydroxy-5-methoxyindole (21)

5-hydroxy-6-methoxyindole (22)

(23)
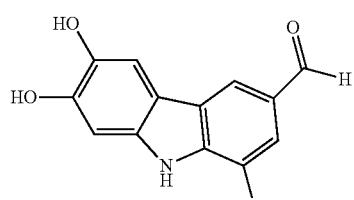
1,6,7-trihydroxy-9H-carbazole-3-carboxaldehyde

(24)
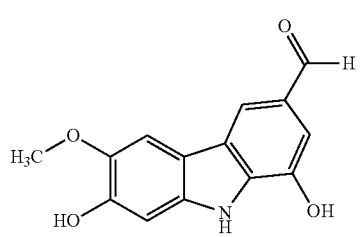
1,7-dihydroxy-6-methoxy-9H-carbazole-3-carboxaldehyde

(25)
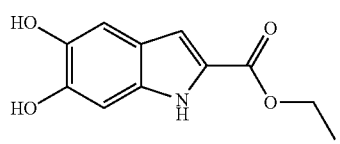
ethyl 5,6-dihydroxy-1H-indole-2-carboxylate

(26)
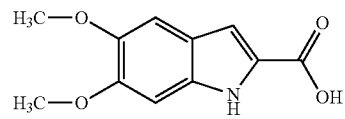
5,6-dimethoxy-1H-indole-2-carboxylate acid

(27)
methyl 5,6-dimethoxy-1H-indole-2-carboxylate

(28)
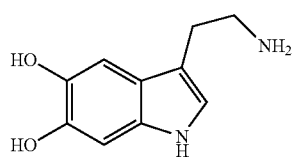
5,6-dihydroxytryptamine

(29)
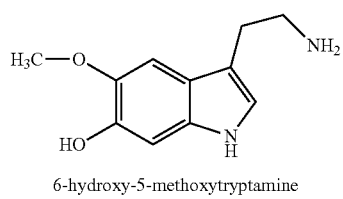
6-hydroxy-5-methoxytryptamine

(30)
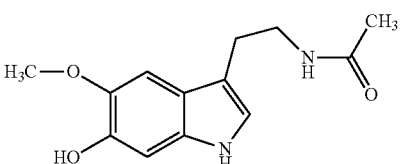
6-hydroxymelatonin

(31)
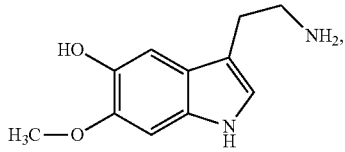
5-hydroxy-6-methoxytryptamine

(32)
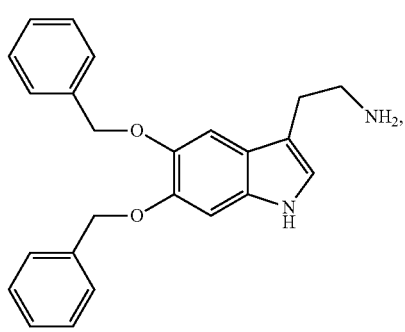
5,6-dibenzoxytryptamine

(33)
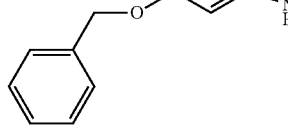
Ancorinolate B

(34)
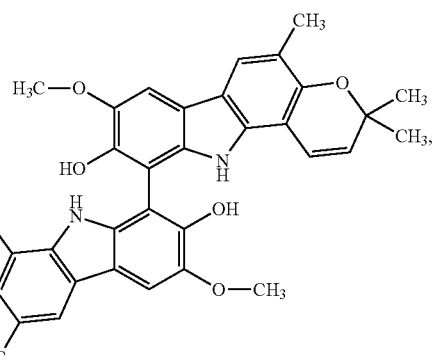
8,8′-bikoenigine

(35)
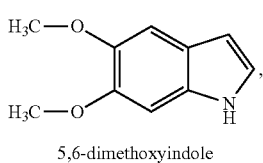
5,6-dimethoxyindole

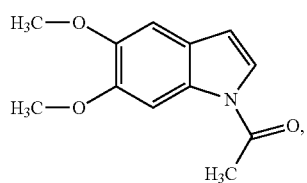

5,6-dimethoxy-1-acetyl-1H-indole

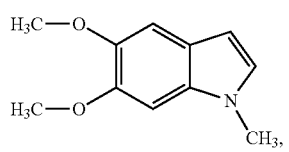

5,6-dimethoxy-1-methyl-1H-indole

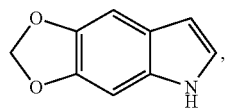

5,6-methylenedioxyindole

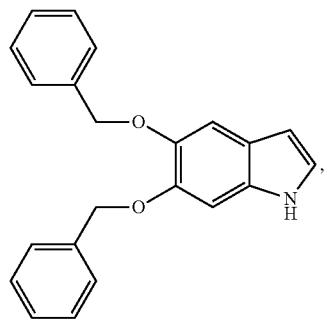

5,6-dibenzoxyindole

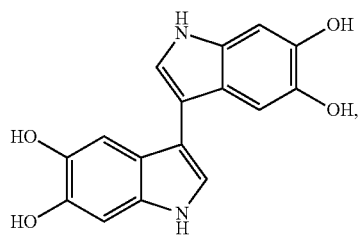

3,3'-bi-1H-indole-5,5',6,6'-tetrol

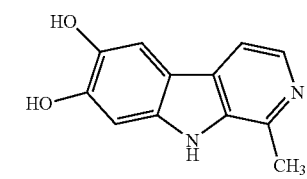

6,7-dihydroxy-1-methyl-β-carboline or 1-methyl-9H-pyrido[3,4-b]indole-6,7-diol

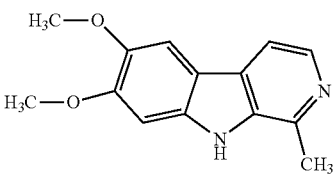

6,7-dimethoxy-1-methyl-β-carboline or 1-methyl-9H-pyrido[3,4-b]indole-6,7-diol

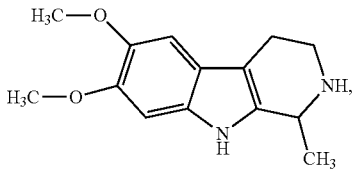

1,2,3,4-tetrahydro-6,7-dimethoxy-1-methyl-β-carboline

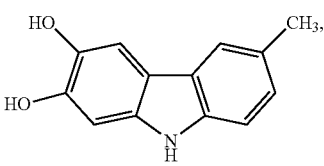

2,3,-dihydroxy-6-methyl-9H-carbazole

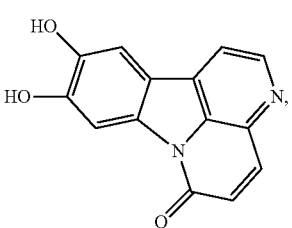

9,10,-dihydroxycanthin-6-one

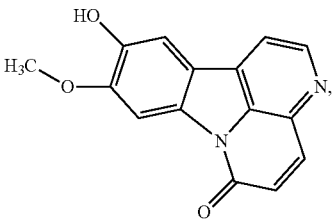

10-hydroxy-9-methoxycanthin-6-one

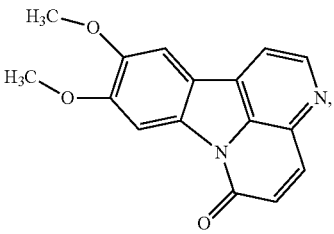

9,10-dimethoxycanthin-6-one

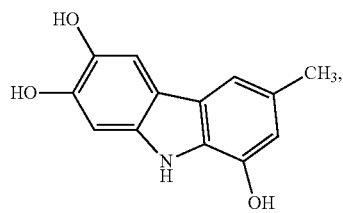

1,6,7-trihydroxy-3-methylcarbazole

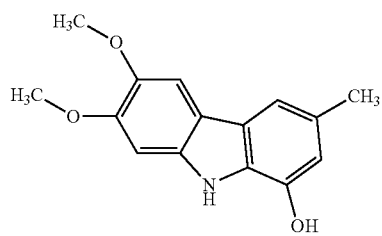

1-hydroxy-6,7-dimethoxy-3-methylcarbazole

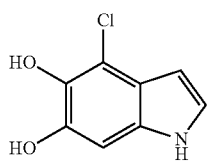

4-chloro-5,6-dihydroxyindole

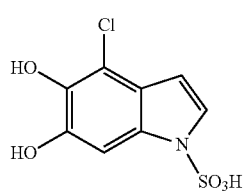

4-chloro-5,6-dihydroxy-1H-indole-1-sulfonic acid

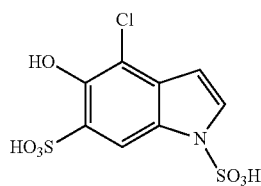

4-chloro-5-hydroxy-1H-indole-1,6-disulfonic acid and also the organic or mineral acid or base salts thereof.

Preferably the compounds of formula (I) are selected from (1) to (9); (15) to (22), (25) to (33), (35) to (39), and (50) to (52) mentioned above; more preferably the compounds of formula (I) are selected from (1) to (9); (15) to (22), (25) to (27), (33), (35) to (39), and (50) to (52) mentioned above.

According to another embodiment of the invention, the compounds of formula (I) are indoline compounds with the ═ bond between the carbon atoms bearing the radicals $R_2$ and $R_3$ representing a single bond.

Preferentially, the indoline compounds that may be used in the dye composition (A) defined above may correspond to formula (Ib) below:

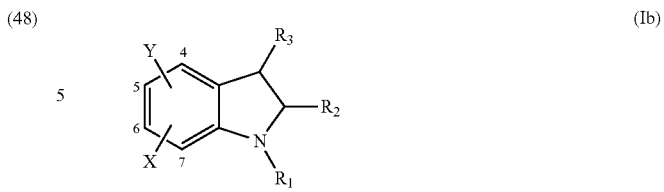

in which formula (Ib) $R_1$, $R_2$, $R_3$, X and Y have the same meanings as those indicated above for the compounds of formula (Ia), and also the enantiomers and diastereoisomers, and the organic or mineral acid or base salts thereof.

Among the preferential indoline compounds of formulae (I) and (Ib), mention may be made of 5,6-dihydroxyindoline, N-methyl-5,6-dihydroxyindoline, N-ethyl-5,6-dihydroxyindoline, N-butyl-5,6-dihydroxyindoline, 4-hydroxy-5-methoxyindoline, 6-hydroxy-7-methoxyindoline, 6,7-dihydroxyindoline, 4,5-dihydroxyindoline and 5-methoxy-6-hydroxyindoline, and the organic or mineral acid or base salts thereof.

According to another embodiment of the invention indoline compounds are chosen from compounds of formula (IV), and its decarboxylated form (IV') and also the enantiomers and diastereoisomers, tautomers and the organic or mineral acid or base salts thereof:

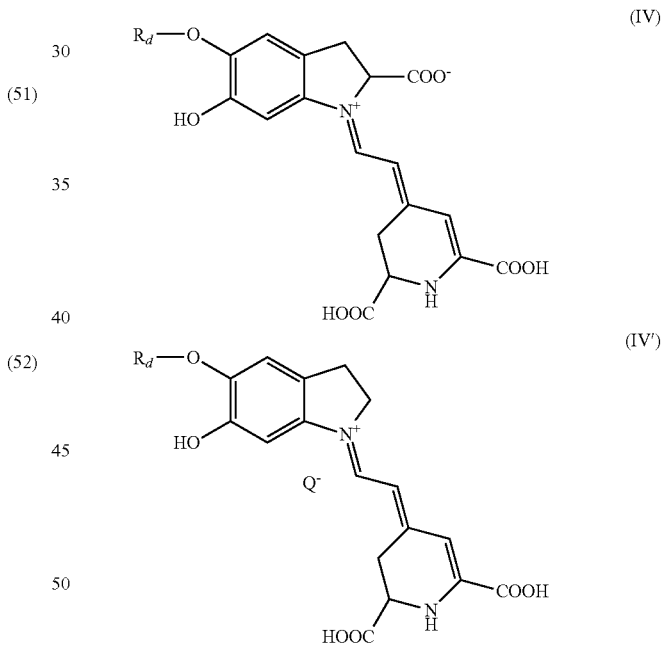

formula (IV) and (IV') in which $R_d$ represents a hydrogen atom (betanidine or betacyanine), a glucosyl radical (betanine), a 6'-O-malonyl-glucosyl radical (phyllocactine), $Q^-$ is an anionic counter ion or is absent if one of the carboxy group is in carboxylate form —COO$^-$.

Preferably, the indole or indoline compounds are chosen from the indole compounds such as compounds (1), (2), (3), (5), (7), (8), (16), (18) and (19) mentioned above, and the indoline compounds such as 5,6-dihydroxyindoline, N-methyl-5,6-dihydroxyindoline, N-ethyl-5,6-dihydroxyindoline, N-butyl-5,6-dihydroxyindoline, 4-hydroxy 5-methoxyindoline, 6-hydroxy-7-methoxyindoline, 6,7-dihydroxyindoline, 4,5-dihydroxyindoline and 5-methoxy 6-hydroxyindoline.

Even more preferentially, the compounds of formula (I) are chosen from 5,6-dihydroxyindole (1) and 5,6-dihydroxyindoline, and also the organic or mineral acid or base salts thereof.

The indole or indoline compounds of the invention may be naturally occurring. The invention may then be performed using one or more natural extracts of animals, bacteria, fungi, algae or plants comprising one or more indole or indoline compounds.

According to a particular embodiment, the compounds i) are selected from (IV) and (IV'), more particularly the compounds i) are derived from an extract of beetroot, especially red beetroot. The extract of red beetroot or *Beta vulgaris* is preferentially an extract obtained from red beetroot, especially from the periphery or outer part of beetroot, more particularly from red beetroot skin or peel (*Eur. Food. Res. Technol.*, Tytti S. Kujala et al., 214, 505-510 (2002)).

The term "red beetroot skin" more particularly denotes the peripheral part of the tuber situated between the epidermis and the pericarp (cf. Hermann et al., *Journal of Experimental Botany*, Vol. 58, No. 11, pp. 3047-3060, 2007).

The extracts are obtained by extracting the various plant parts, for instance the root, the leaves or the peel. Preferentially, the extract is obtained from extraction of red beetroot peel.

The extraction is performed via standard methods known to those skilled in the art. Mention may be made, for example, of the method described in *Eur. Food. Res. Technol.*, Tytti S. Kujala et al., 214, 505-510 (2002)).

The natural red beetroot extracts according to the invention may be in the form of powders or liquids. Preferentially, the extracts of the invention are in the form of powders, such as red beetroot peel extract powders.

According to the invention, the red beetroot extract(s) used as ingredient i) in one or more composition(s) that are useful in the process according to the invention preferably represent from 0.001% to 20% by weight relative to the total weight of the composition(s) containing said extract(s).

According to the invention, the indole and/or indoline compound(s) as defined previously are preferably present in a concentration ranging from 0.0005% to 10% by weight relative to the total weight of the dye composition (A). Even more preferentially, this concentration ranges from 0.005% to 5% by weight and better still from 0.01% to 3% by weight, relative to the total weight of the dye composition (A).

For the purposes of the present invention, and unless otherwise indicated:

The saturated or unsaturated and optionally fused rings can also be optionally substituted.

The "alkyl" radicals are saturated, linear or branched, generally $C_1$-$C_{20}$ and particularly $C_1$-$C_{10}$ hydrocarbon-based radicals, preferably $C_1$-$C_6$ alkyl radicals, such as methyl, ethyl, propyl, butyl, pentyl and hexyl.

The "alkenyl" radicals are linear or branched, unsaturated $C_2$-$C_{20}$ hydrocarbon-based radicals; preferably comprising one or more conjugated or unconjugated double bonds, such as ethylene, propylene, butylene, pentylene, 2-methylpropylene, decylene and =CH—CH=.

The "aryl" radicals are fused or non-fused monocyclic or polycyclic carbon-based radicals, preferentially comprising from 6 to 30 carbon atoms, and of which at least one ring is aromatic; the aryl radical is preferentially a phenyl, biphenyl, naphthyl, indenyl, anthracenyl or tetrahydronaphthyl.

The "alkoxy" radicals are alkyl-oxy radicals with alkyl as defined previously, preferably $C_1$-$C_{10}$ alkyl, such as methoxy, ethoxy, propoxy and butoxy.

The "alkoxyalkyl" radicals are preferably ($C_1$-$C_{20}$)alkoxy ($C_1$-$C_{20}$)alkyl radicals, such as methoxymethyl, ethoxymethyl, methoxyethyl, ethoxyethyl, and the like.

The "cycloalkyl" radicals are generally $C_4$-$C_8$ cycloalkyl radicals, preferably the cyclopentyl and cyclohexyl radicals. The cycloalkyl radicals can be substituted cycloalkyl radicals, in particular substituted by alkyl, alkoxy, carboxylic acid, hydroxyl, amine and ketone groups.

The "alkyl" or "alkenyl" radicals, when they are optionally substituted, may be substituted with at least one substituent borne by at least one carbon atom, chosen from:
  a halogen atom;
  a hydroxyl group;
  a $C_1$-$C_2$ alkoxy radical;
  a $C_1$-$C_{10}$ alkoxycarbonyl radical;
  a $C_2$-$C_4$ (poly)hydroxyalkoxy radical;
  an amino radical;
  a quaternary ammonium group —N$^+$R'R"R''', M$^-$ for which R', R" and R''', which may be identical or different, represent a hydrogen atom or a $C_1$-$C_4$ alkyl group; and M$^-$ represents the counterion of the corresponding organic or mineral acid or the halide;
  a 5- or 6-membered heterocycloalkyl radical;
  an optionally cationic 5- or 6-membered heteroaryl radical, preferentially imidazolium, optionally substituted with a ($C_1$-$C_4$)alkyl radical, preferentially methyl;
  an amino radical substituted with one or two identical or different $C_1$-$C_6$ alkyl radicals optionally bearing at least:
    a hydroxyl group;
    an amino group optionally substituted with one or two optionally substituted $C_1$-$C_3$ alkyl radicals, it being possible for said alkyl radicals to form, with the nitrogen atom to which they are attached, a saturated or unsaturated and optionally substituted 5- to 7-membered heterocycle optionally comprising at least one other nitrogen or non-nitrogen heteroatom;
    a quaternary ammonium group —N$^+$R'R"R''', M$^-$ as defined previously;
    or an optionally cationic 5- or 6-membered heteroaryl radical, preferentially imidazolium, optionally substituted with a ($C_1$-$C_4$)alkyl radical, preferentially methyl;
  an acylamino radical (—NR—C(O)R') in which the radical R is a hydrogen atom, a $C_1$-$C_4$ alkyl radical optionally bearing at least one hydroxyl group and the radical R' is a $C_1$-$C_2$ alkyl radical; a carbamoyl radical ((R)$_2$N—C(O)—) in which the radicals R, which may be identical or different, represent a hydrogen atom, a $C_1$-$C_4$ alkyl radical optionally bearing at least one hydroxyl group; an alkylsulfonylamino radical (R'S(O)$_2$—NR—) in which the radical R represents a hydrogen atom, a $C_1$-$C_4$ alkyl radical optionally bearing at least one hydroxyl group and the radical R' represents a $C_1$-$C_4$ alkyl radical or a phenyl radical; an aminosulfonyl radical ((R)$_2$N—S(O)$_2$— in which the radicals R, which may be identical or different, represent a hydrogen atom or a $C_1$-$C_4$ alkyl radical optionally bearing at least one hydroxyl group;
  a carboxyl radical in the acid or salified form (preferably in the form salified with an alkali metal or a substituted or unsubstituted ammonium);
  a cyano group;
  a nitro group;
  a carboxyl or glycosylcarbonyl group;
  a phenylcarbonyloxy group optionally substituted with one or more hydroxyl groups;

a glycosyloxy group; and a phenyl group optionally substituted with one or more hydroxyl groups.

The "aryl" or "heteroaryl" or "heterocyclic" radicals or the "aryl" or "heteroaryl" or "heterocyclic" part of the radicals, when they are optionally substituted, may be substituted with at least one substituent borne by at least one carbon atom, chosen from:

a $C_1$-$C_{10}$ and preferably $C_1$-$C_8$ alkyl radical optionally substituted with one or more radicals chosen from the following radicals: hydroxyl, $C_1$-$C_2$ alkoxy, $C_2$-$C_4$ (poly)hydroxyalkoxy, acylamino, amino substituted with two $C_1$-$C_4$ alkyl radicals, which may be identical or different, optionally bearing at least one hydroxyl group, or the two radicals possibly forming, with the nitrogen atom to which they are attached, a saturated or unsaturated, optionally substituted 5- to 7-membered and preferably 5- or 6-membered heterocycle optionally comprising another nitrogen or non-nitrogen heteroatom;

a halogen atom;

a hydroxyl group;

a $C_1$-$C_2$ alkoxy radical;

a $C_1$-$C_{10}$ alkoxycarbonyl radical;

a $C_2$-$C_4$ (poly)hydroxyalkoxy radical;

an amino radical;

a 5- or 6-membered heterocycloalkyl radical;

an optionally cationic 5- or 6-membered heteroaryl radical, preferentially imidazolium, optionally substituted with a ($C_1$-$C_4$)alkyl radical, preferentially methyl;

an amino radical substituted with one or two identical or different $C_1$-$C_6$ alkyl radicals optionally bearing at least:

a hydroxyl group;

an amino group optionally substituted with one or two optionally substituted $C_1$-$C_3$ alkyl radicals, it being possible for said alkyl radicals to form, with the nitrogen atom to which they are attached, a saturated or unsaturated and optionally substituted 5- to 7-membered heterocycle optionally comprising at least one other nitrogen or non-nitrogen heteroatom;

a quaternary ammonium group —$N^+R'R''R'''$, $M^-$ for which R', R" and R'", which may be identical or different, represent a hydrogen atom or a $C_1$-$C_4$ alkyl group; and $M^-$ represents the counterion of the corresponding organic or mineral acid or of the corresponding halide;

or an optionally cationic 5- or 6-membered heteroaryl radical, preferentially imidazolium, optionally substituted with a ($C_1$-$C_4$)alkyl radical, preferentially methyl;

an acylamino radical (—NR—C(O)R') in which the radical R is a hydrogen atom, a $C_1$-$C_4$ alkyl radical optionally bearing at least one hydroxyl group and the radical R' is a $C_1$-$C_2$ alkyl radical; a carbamoyl radical (($R)_2$N—CO—) in which the radicals R, which may be identical or different, represent a hydrogen atom, a $C_1$-$C_4$ alkyl radical optionally bearing at least one hydroxyl group; an alkylsulfonylamino radical (R'S(O)$_2$—NR—) in which the radical R represents a hydrogen atom, a $C_1$-$C_4$ alkyl radical optionally bearing at least one hydroxyl group and the radical R' represents a $C_1$-$C_4$ alkyl radical or a phenyl radical; an aminosulfonyl radical (($R)_2$N—S(O)$_2$—) in which the radicals R, which may be identical or different, represent a hydrogen atom or a $C_1$-$C_4$ alkyl radical optionally bearing at least one hydroxyl group;

a carboxyl radical in the acid or salified form (preferably in the form salified with an alkali metal or a substituted or unsubstituted ammonium);

a cyano group;

a nitro group;

a polyhaloalkyl group, preferentially trifluoromethyl;

a carboxyl or glycosylcarbonyl group;

a phenylcarbonyloxy group optionally substituted with one or more hydroxyl groups;

a glycosyloxy group; and a phenyl group optionally substituted with one or more hydroxyl groups.

The term "glycosyl radical" is understood to mean a radical resulting from a monosaccharide or polysaccharide.

The radicals comprising one or more silicon atoms are preferably polydimethylsiloxane, polydiphenylsiloxane, polydimethylphenylsiloxane or stearoxy dimethicone radicals.

The "heterocyclic" radicals are generally cyclic, saturated or unsaturated 3- to 22-membered radicals, comprising in at least one ring one or more heteroatoms chosen from O, N and S, preferably O or N, optionally substituted especially with one or more alkyl, alkoxy, carboxylic acid, hydroxyl, amine or ketone groups. These rings may contain one or more oxo groups on the carbon atoms of the heterocycle of the non-aromatic part. The heterocycles include heteroaryl, heterocycloalkyl or heterocycloalkenyl groups.

The "heterocycloalkyl" radicals represent saturated monocyclic or polycyclic, fused or non-fused, optionally cationic, 3- to 22-membered and preferentially 3- to 7-membered groups, such as morpholinyl, thiomorpholinyl, piperidyl, piperazinyl, pyrrolidinyl, tetrahydrofuryl or azepanyl, preferentially pyrrolidinyl and morpholinyl;

The "heterocycloalkenyl" radicals represent unsaturated monocyclic or polycyclic, fused or non-fused, optionally cationic, 3- to 22-membered and preferentially 5- to 7-membered groups, which comprise from 1 to 3 conjugated or unconjugated double bonds; particularly, the heterocloalkenyls are piperazenyl such as piperazin-2-en-4-yl, optionally substituted especially with two carboxyl groups in positions 2 and 6 of said heterocycloalkenyl;

The "heteroaryl" radicals represents fused or non-fused, optionally cationic, 5- to 22-membered monocyclic or polycyclic groups, comprising from 1 to 6 heteroatoms chosen from nitrogen, oxygen, sulfur and selenium atoms, and at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridyl, tetrazolyl, di hydrothiazolyl, imidazopyridyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridyl, thiazoylimidazolyl, thiopyrylyl, triazolyl, xanthyl and the ammonium salt thereof;

Among the "heterocyclic" radicals that may be used, mention may be made of the furyl, pyranyl, pyrrolyl, imidazolyl, pyrazolyl, pyridyl and thienyl groups.

More preferably, the "heterocyclic" groups are fused groups, such as benzofuryl, chromenyl, xanthenyl, indolyl, isoindolyl, quinolyl, isoquinolyl, chromanyl, isochromanyl, indolinyl, isoindolinyl, coumarinyl or isocoumarinyl groups, these groups possibly being substituted, in particular by one or more OH groups.

The term "salt of an organic or mineral acid" means a salt derived, for example, from i) hydrochloric acid HCl, ii) hydrobromic acid HBr, iii) sulfuric acid $H_2SO_4$, iv) alkylsulfonic acids: Alk-$S(O)_2$OH such as methanesulfonic acid and ethanesulfonic acid; v) arylsulfonic acids: Ar—$S(O)_2$OH such as benzenesulfonic acid and toluenesulfonic acid; vi) citric acid; vii) succinic acid; viii) tartaric acid; ix) lactic acid; x) alkoxysulfinic acids: Alk-O—S(O)OH such as methoxysulfinic acid and ethoxysulfinic acid; xi) aryloxysulfinic acids such as tolueneoxysulfinic acid and phenoxysulfinic acid; xii) phosphoric acid $P(O)(OH)_3$; xiii) acetic acid $CH_3C(O)OH$; xiv) triflic acid $CF_3S(O)_2OH$; and xv) tetrafluoroboric acid $HBF_4$.

The term "salt of an organic or mineral base" means a salt derived, for example, from mineral bases such as i) sodium hydroxide NaOH, ii) potassium hydroxide KOH, or from organic bases such as iii) aqueous ammonia; iv) amines and hydroxyamines such as (tri)($C_1$-$C_6$)alkylamine, (tri)hydroxy($C_1$-$C_6$)alkylamine; or v) salts derived from alkali metals and alkaline-earth metals.

The term "contiguous group" refers to two substituents that are next to each other, in the ortho position, on an aromatic group.

The "anionic counterions" are anions or anionic groups associated with the cationic charge of the dye; more particularly, the anionic counterion is chosen from: i) halides such as chloride or bromide; ii) nitrates; iii) sulfonates, including $C_1$-$C_6$ alkylsulfonates: Alk-$S(O)_2O^−$ such as methanesulfonate or mesylate and ethanesulfonate; iv) arylsulfonates: Ar—$S(O)_2O^−$ such as benzenesulfonate and toluenesulfonate or tosylate; v) citrate; vi) succinate; vii) tartrate; viii) lactate; ix) alkyl sulfates: Alk-O—$S(O)O^−$ such as methyl sulfate and ethyl sulfate; x) aryl sulfates: Ar—O—$S(O)O^−$ such as benzene sulfate and toluene sulfate; xi) alkoxy sulfates: Alk-O—$S(O)_2O^−$ such as methoxy sulfate and ethoxy sulfate; xii) aryloxy sulfates: Ar—O—$S(O)_2O^−$; xiii) phosphate; xiv) acetate; xv) triflate; and xvi) borates such as a tetrafluoroborate.

ii) Aromatic Compound(s) Comprising a Hydrocarbon-Based Polycycle Containing at Least 10 Carbon Atoms The aromatic compound(s) ii) which comprise a hydrocarbon-based polycycle comprising at least 10 carbon atoms, according to the invention, are aromatic compounds comprising a hydrocarbon-based polycycle comprising at least 10 carbon atoms, at least one of the rings of which is aromatic. The aromatic compound(s) ii) may be substituted with one or more groups as defined previously for the substituents of the "aryl" groups. The substituent(s) of the aromatic compound(s) are particularly chosen from hydroxyl and amino groups, preferably hydroxyl. Preferentially, the hydroxyl groups are not contiguous.

According to a particular embodiment, the polycycle comprises only aromatic rings. More particularly, the polycycle comprises from 10 to 30 carbon atoms. Preferentially, the polycycle is a bicycle comprising 10 carbon atoms. Even more preferentially, this polycycle is monohydroxylated or polyhydroxylated and may be chosen especially from (di)hydroxynaphthalenes, particularly dihydroxynaphthalenes such as 2,7-dihydroxynaphthalene.

According to a particular embodiment the aromatic compounds ii) correspond to the following formula (II):

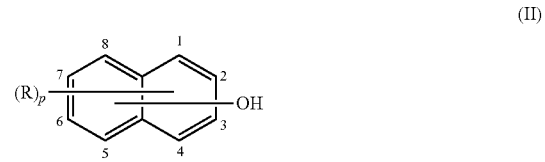

(II)

and also the organic or mineral acid or base salts thereof, optical isomers thereof: enantiomers and diastereoisomers, geometrical isomers and tautomers thereof, and solvates thereof such as hydrates;

Formula (II) wherein

R, identical or different, represent a halogen atom, or a ($C_1$-$C_6$)alkyl group, ($C_1$-$C_6$)alkoxy group, ($C_1$-$C_6$) alkylthio, (di) ($C_1$-$C_6$)(alkyl)amino group, hydroxyl group, thio, heterocyclic group such as morpholinyl group, pyperidinyl group, or ($C_1$-$C_6$)(alkyl)piperazinyl group preferably R is(are) selected from hydroxy or ($C_1$-$C_6$)alkyl group;

p represents 0, 1, 2, 3, 4, 5, 6 or 7, particularly p=0, 1 or 2 preferably p=0 or 1, more preferably p=1.

According to a preferred embodiment compounds of formula (II) are with R located on carbon atom 2, 5 or 7 and OH is located preferably on carbon atom 1 or 2 being understood that R and OH cannot be located simultaneously on the same carbon atom of the naphtalen.

Preferably ingredient ii) is selected from: 2,7-Naphthalenediol; 1,5-Naphthalenediol; 1-Hydroxy-naphthalene; and 2-Methyl-1-naphthol, more preferably 1-Hydroxy-naphthalene or 1-naphtol.

Additional Ortho-Diphenol(s)

In the process of the invention, the indole and/or indoline compounds as defined previously may be used in combination with ortho-diphenols, other than the ingredients i) and ii) as defined previously, comprising at least one aromatic ring, preferably a benzene ring, comprising at least two hydroxyl groups (OH) borne by two adjacent carbon atoms of the aromatic ring.

The "aromatic ring" may more particularly be a fused "aryl" or fused "heteroaryl" ring, i.e. optionally containing one or more heteroatoms, such as benzene, naphthalene, tetrahydronaphthalene, indane, indene, anthracene, phenanthrene, isoindole, isoindoline, benzofuran, dihydrobenzofuran, chroman, isochroman, chromene, isochromene, quinoline, tetrahydroquinoline and isoquinoline, said aromatic ring comprising at least two hydroxyl groups borne by two adjacent carbon atoms of the aromatic ring. Preferentially, the aromatic ring of the ortho-diphenol derivatives according to the invention is a benzene ring.

The term "fused ring" is understood to mean that at least two saturated or unsaturated and heterocyclic or non-heterocyclic rings exhibit a common bond, i.e. that at least one ring is placed side by side with another ring.

The additional ortho-diphenols according to the invention may or may not be salified. They can also be in the aglycone form (without bonded sugar) or in the form of glycosylated compounds.

More particularly, the ortho-diphenol derivatives represent compounds of formula (V), other than the indole and indoline compounds as defined previously, or an oligomer thereof, in salified or non-salified form:

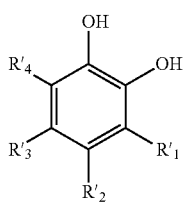

in which formula (V) the substituents:
R'$_1$ to R'$_4$, which may be identical or different, represent:
a hydrogen atom,
a halogen atom,
a hydroxyl radical,
a carboxyl radical,
an alkyl carboxylate or alkoxycarbonyl radical,
an optionally substituted amino radical,
an optionally substituted and linear or branched alkyl radical,
an optionally substituted and linear or branched alkenyl radical,
an optionally substituted cycloalkyl radical,
an alkoxy radical,
an alkoxyalkyl radical,
an alkoxyaryl radical, the aryl group possibly being optionally substituted,
an aryl radical,
a substituted aryl radical,
a saturated or unsaturated heterocyclic radical, optionally bearing a cationic or anionic charge, optionally substituted and/or optionally fused with an aromatic ring, preferably a benzene ring, said aromatic ring being optionally substituted particularly with one or more hydroxyl or glycosyloxy groups,
a radical containing one or more silicon atoms,
in which two substituents borne by two adjacent carbon atoms R'$_1$—R'$_2$, R'$_2$—R'$_3$ or R'$_3$—R'$_4$ form, together with the carbon atoms bearing them, a saturated or unsaturated, aromatic or non-aromatic ring optionally containing one or more heteroatoms and optionally fused with one or more saturated or unsaturated rings optionally containing one or more heteroatoms, it being understood that R'$_1$—R'$_2$, R'$_2$—R'$_3$ or R'$_3$—R'$_4$ cannot form with the carbon atoms that bear them a pyrrolyl or pyrrolidinyl radical.

A particular embodiment of the invention relates to ortho-diphenol derivatives of formula (V) in which two substituents are adjacent.

The additional ortho-diphenols that are useful in the process of the invention may be natural or synthetic. Among the additional natural ortho-diphenols are compounds that may be present in nature and that are reproduced by chemical (semi)synthesis.

The salts of the ortho-diphenols of the invention can be salts of acids or of bases. The acids may be mineral or organic. Preferably, the acid is hydrochloric acid, which results in chlorides.

The bases may be mineral or organic. In particular, the bases are alkali metal hydroxides, such as sodium hydroxide, which results in sodium salts.

According to a specific embodiment of the invention, the composition comprises, as additional ingredient, one or more synthetic ortho-diphenol derivative(s) which do not exist in nature.

More particularly, the additional ortho-diphenols that may be used in the process of the invention are in particular:
flavanols, for instance catechin and epicatechin gallate,
flavonols, such as quercetin,
anthocyanidins, such as cyanidin, delphinidin or petunidin,
anthocyanins or anthocyans, such as myrtillin,
ortho-hydroxybenzoates, for example gallic acid salts,
flavones, such as luteolin,
hydroxystilbenes, for example 3,3',4,5'-tetrahydroxystilbene, optionally oxylated (for example glucosylated),
3,4-dihydroxyphenylalanine and derivatives thereof,
2,3-dihydroxyphenylalanine and derivatives thereof,
4,5-dihydroxyphenylalanine and derivatives thereof,
dihydroxycinnamates, such as caffeic acid and chlorogenic acid,
ortho-polyhydroxycoumarins,
ortho-polyhydroxyisocoumarins,
ortho-polyhydroxycoumarones,
ortho-polyhydroxyisocoumarones,
ortho-polyhydroxychalcones,
ortho-polyhydroxychromones,
ortho-polyhydroxyquinones,
ortho-polyhydroxyxanthones,
1,2-dihydroxybenzene and derivatives thereof,
1,2,4-trihydroxybenzene and derivatives thereof,
1,2,3-trihydroxybenzene and derivatives thereof,
2,4,5-trihydroxytoluene and derivatives thereof,
proanthocyanidins and in particular the proanthocyanidins A1, A2, B1, B2, B3 and C1,
proanthocyanins,
tannic acid,
ellagic acid,
ortho-hydroxycoumestanes,
ortho-hydroxypterocarpanes,
ortho-hydroxyneoflavans
and the mixtures of the preceding compounds.

When the dye precursors exhibit D and L forms, both forms can be used in the compositions according to the invention, as can the racemates.

According to one embodiment, the additional natural ortho-diphenols are derived from extracts of animals, bacteria, fungi, algae or plants, used in their entirety or partially. In particular as regards plants, the extracts result from plants or plant parts, such as fruit, including citrus fruit, vegetables, trees or shrubs. Use may also be made of mixtures of these extracts, which are rich in ortho-diphenols as defined above.

Preferably, the additional natural ortho-diphenol(s) of the invention are derived from extracts of plants or plant parts.

For the purposes of the invention, these said extracts will be put, in their entirety, into the same category as additional ortho-diphenol or ingredient.

The extracts are obtained by extraction of various plant parts, for instance the root, the wood, the bark, the leaf, the flower, the fruit, the seed, the pod or the peel.

Among the plant extracts, mention may be made of extracts of tea and rose leaves, extracts of rosemary leaves and extracts of mate leaves.

Among the fruit extracts, mention may be made of extracts of apple, of grape (in particular of grape seed) or extracts of cocoa beans and/or pods.

Among the vegetable extracts, mention may be made of extracts of potato or of onion peel.

Among the extracts of tree wood, mention may be made of extracts of pine bark, extracts of campeachy wood, extracts of quebracho wood, extracts of brazilleto wood and extracts of gall nuts.

Preferably, the natural ortho-diphenol(s) of the invention are derived from extracts of plants or plant parts.

The extracts are obtained by extraction of various plant parts, for instance the root, the wood, the bark, the leaf, the flower, the fruit, the seed, the pod or the peel.

Use may also be made of mixtures of plant extracts.

According to one particular embodiment of the invention, the additional ortho-diphenol derivative(s) are natural extracts, rich in ortho-diphenols. According to one preferred mode, the additional ortho-diphenol derivative(s) are solely natural extracts.

According to a particularly preferred embodiment of the invention, the additional ortho-diphenol(s) as defined previously are also natural extracts.

The natural extracts according to the invention may be in the form of powders or liquids. Preferably, the extracts of the invention are provided in the form of powders.

According to the invention, the synthetic, natural ortho-diphenol derivative(s), and/or the natural extract(s) used containing them preferably represent from 0.001% to 20% by weight relative to the total weight of composition (A).

As regards the pure additional ortho-diphenols, the content in composition (A) containing them is preferably between 0.001% and 5% by weight of this composition.

As regards the extracts, the content in composition (A) containing the extracts per se is preferably between 0.5% and 20% by weight of this composition.

iii) Metal Salt(s)

According to a particular embodiment of the invention, the process of the invention uses one or more ingredients iii) that are metal salts.

Preferentially, the metal salts used in the dyeing process or in the composition of the invention are chosen from transition metal salts, such as manganese salts, and rare-earth metal salts, such as cerium salts, and also mixtures thereof. Particularly, the metal salts are chosen from transition metal and more particularly chosen from Iron (Fe), manganese (Mn) and zinc (Zn) salts, preferably manganese (Mn) and zinc (Zn) salts and more preferably Mn.

The metal salts may be mineral or organic salts.

According to one variant, the metal salts are mineral and may be chosen from halides such as chlorides, fluorides and iodides, carbonates, sulfates and phosphates, especially optionally hydrated halides.

According to an advantageous variant of the invention, the metal salt(s) are organic and are preferentially chosen from carboxylic acid salts and polymer complexes that can support said salts, and also mixtures thereof.

The metal catalysts are particularly chosen from organic acid salts of transition metals, especially of manganese, and mineral salts of rare-earth metals, especially of cerium.

According to a particular embodiment of the invention, manganese is different from a manganese oxide, more particularly iii) is a manganese salt.

According to another particular embodiment of the invention iii) represents zinc salts and preferably selected from zinc sulfate, zinc gluconate, zinc chloride, zinc lactate, zinc acetate, zinc glycinate, and zinc aspartate.

The manganese and zinc salts may be introduced in solid form into the compositions or may be derived from a natural, mineral or thermal water that is rich in these ions or alternatively from seawater (especially the Dead Sea). They may also originate from mineral compounds, for instance earths, ochres such as clays (for example green clay) or even from a plant extract containing them (cf. for example patent FR 2 814 943).

As examples of polymer complexes that can support said polymer salts, mention may be made of manganese pyrrolidonecarboxylate.

According to a preferred variant, the metal salts are in oxidation state II and bear two (poly)hydroxy acid-based ligands.

The term "(poly)hydroxy acid" means any carboxylic acid which comprises a hydrocarbon-based chain which is linear or branched, and saturated or unsaturated, preferably saturated and/or linear, comprising from 1 to 10 carbon atoms and from 1 to 9 hydroxyl groups, and comprising from 1 to 4 carboxylic groups —C(O)—OH, at least one of said —C(O)—OH functions of which is in the carboxylate form —C(O)—O⁻ complexed with the metal atom, preferably Mn(II). More particularly, the metal salt is complexed with two carboxylate groups such as that of formula (VI):

and also the solvates thereof, such as hydrates, and enantiomers thereof, in which formula (VI):

M represents a metal (II) or metal$^{2+}$ in oxidation state 2, such as Zn or Mn, preferably Mn;

R and R', which may be identical or different, represent a ($C_1$-$C_6$)(poly)hydroxyalkyl group.

The organic metal salts may be more particularly chosen from organic acid salts such as citrates, lactates, glycolates, gluconates, acetates, propionates, fumarates, oxalates and tartrates, especially gluconates.

More particularly, the manganese salt is other than manganese carbonate, manganese hydrogen carbonate or manganese dihydrogen carbonate.

Preferably, the metal salt(s) are chosen from the compounds of formula (VI) and more particularly represent manganese gluconate.

The metal catalysts may be present in a content ranging from 0.001% to 10% by weight, preferably in a content ranging from 0.001% to 1% by weight, better still ranging from 0.01% to 0.5% by weight relative to the total weight of the composition.

Composition (A) may contain additional ingredients: see "Additional ingredients or adjuvants" below.

This composition (A) may be anhydrous or aqueous, preferably aqueous.

iv) Hydrogen Peroxide or Hydrogen Peroxide-Generating System(s)

According to a particular embodiment, the process uses iv) hydrogen peroxide or one or more hydrogen peroxide-generating systems such as:

a) urea peroxide;
b) polymeric complexes that can release hydrogen peroxide, such as polyvinylpyrrolidone/$H_2O_2$ in particular in the form of powders, and the other polymeric complexes described in U.S. Pat. Nos. 5,008,093; 3,376,110; 5,183,901;
c) oxidases that produce hydrogen peroxide in the presence of a suitable substrate (for example glucose in the case of glucose oxidase or uric acid with uricase);
d) metal peroxides that generate hydrogen peroxide in water, for instance calcium peroxide or magnesium peroxide;
e) perborates; or
f) percarbonates.

According to a preferred embodiment of the invention, composition (A) contains hydrogen peroxide or one or more hydrogen peroxide-generating system(s), chosen from a) urea peroxide, b) polymeric complexes that can release hydrogen peroxide, chosen from polyvinylpyrrolidone/ $H_2O_2$; c) oxidases; e) perborates and f) percarbonates.

In particular, compound iv) is hydrogen peroxide.

According to a particular embodiment of the invention, the hydrogen peroxide or the hydrogen peroxide-generating system(s) used preferably represent(s) from 0.001% to 12% by weight, expressed as hydrogen peroxide, relative to the total weight of the composition containing them, and even more preferentially from 0.2% to 2.7% by weight.

v) Basifying Agent(s)

According to a particular embodiment, the dyeing process of the invention uses a composition (B) which comprises one or more basifying agents.

The basifying agent(s) may be mineral or organic.

Among the organic basifying agents, mention may be made of organic amines and in particular alkanolamines such as monoethanolamine (MEA), diethanolamine, triethanolamine, 2-amino-2-methyl-1-propanol, amino acids, in particular basic amino acids such as lysine and arginine, and optionally substituted alkylenediamines of formula (VII) below:

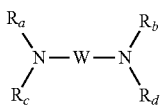

(VII)

in which formula (VII) W is a propylene residue optionally substituted with a hydroxyl group or a $C_1$-$C_4$ alkyl radical; $R_a$, $R_b$, $R_c$ and $R_d$, which may be identical or different, represent a hydrogen atom or a $C_1$-$C_4$ alkyl or $C_1$-$C_4$ hydroxyalkyl radical, for instance diamine compounds such as diaminopropane.

Particularly, the organic basifying agent(s) are chosen from basic amino acids, especially arginine. Preferably the organic basifying agent(s) are chosen from alkanolamines, and in particular monoethanolamine. Among the mineral basifying agents, mention may be made of ammonia, alkali metal or alkaline-earth metal hydroxides, phosphates, monohydrogen phosphates and (bi)carbonates.

In the context of the present invention, the preferred basifying agent is chosen from (bi)carbonates.

The term "(bi)carbonates" is understood to mean:
a) carbonates of alkali metals ($Met_2^+$, $CO_3^{2-}$), of alkaline-earth metals ($Met'^{2+}$, $CO_3^{2-}$) of ammonium (($R''_4N^+)_2$, $CO_3^{2-}$) or of phosphonium (($R''_4P^+)_2$, $CO_3^{2-}$ with Met' representing an alkaline-earth metal and Met representing an alkali metal, and R'', which may be identical or different, represent a hydrogen atom or an optionally substituted ($C_1$-$C_6$)alkyl group such as hydroxyethyl); and
b) bicarbonates, also known as hydrogen carbonates, of the following formulae:
$R'^+$, $HCO_3^-$ with $R'^+$ representing a hydrogen atom, an alkali metal, an ammonium group $R''_4N^+$ or a phosphonium group $R''_4P^+$ where R'', which may be identical or different, represent a hydrogen atom or an optionally substituted ($C_1$-$C_6$)alkyl group, such as hydroxyethyl, and, when R' represents a hydrogen atom, the hydrogen carbonate is then known as dihydrogen carbonate ($CO_2$, $H_2O$); and
$Met_2^+(HCO_3^{2-})$ with Met representing an alkali metal, or $Met'^{2+}(HCO_3^-)_2$ with Met' representing an alkaline-earth metal.

More particularly, the mineral basifying agent is chosen from alkali metal or alkaline-earth metal (bi)carbonates, preferentially alkali metal (bi)carbonates.

Mention may be made of Na, K, Mg and Ca carbonates or hydrogen carbonates and mixtures thereof, and in particular sodium hydrogen carbonate. These hydrogen carbonates may originate from a natural water, for example spring water from the Vichy basin or from La Roche Posay or Badoit water (cf. for example, patent FR 2 814 943). Mention may in particular be made of sodium carbonate [497-19-8]= $Na_2CO_3$, sodium hydrogen carbonate or sodium bicarbonate [144-55-8]=$NaHCO_3$, and sodium dihydrogen carbonate=$Na(HCO_3)_2$.

In a first particular variant of the invention, composition (B) comprises one or more mineral basifying agents.

In a second particular variant of the invention, composition (B) comprises one or more mineral basifying agents and one or more organic basifying agents.

More preferably, composition (B) comprises as ingredient v) one or more (bi)carbonates and/or one or more alkanolamines such as monoethanolamine (MEA).

According to the invention, the basifying agent(s) used preferably represent from 0.001% to 10% by weight relative to the total weight of composition (B), and even more preferentially from 0.005% to −10% by weight, even more preferably from 0.005% to −5%.

Cosmetic Composition(s):

The compositions according to the invention are preferably aqueous.

They may also comprise one or more organic solvents.

The term "organic solvent" means an organic substance that is capable of dissolving or dispersing another substance without chemically modifying it.

The Organic Solvents:

Examples of organic solvents that may be mentioned include $C_1$-$C_4$ lower alkanols, such as ethanol and isopropanol; polyols and polyol ethers such as 2-butoxyethanol, propylene glycol, propylene glycol monomethyl ether, diethylene glycol monoethyl ether, diethylene glycol monomethyl ether, hexylene glycol, and also aromatic alcohols, such as benzyl alcohol or phenoxyethanol.

The organic solvents may be present in proportions preferably of between 1% and 40% by weight approximately, and even more preferentially between 5% and 30% by weight approximately, relative to the total weight of the composition containing them.

Another subject of the invention is a dye composition for dyeing human keratin fibres, comprising i) one or more indole or indoline compounds as defined previously; and ii) one or more aromatic compounds comprising a hydrocarbon-based polycycle comprising at least 10 carbon atoms, at least one of the rings of which is aromatic, as defined previously, chosen especially from (di)hydroxynaphthalenes such as 2,7-dihydroxynaphthalene.

According to a particular embodiment, the dye composition as defined previously also comprises iii) one or more metal salts as defined previously.

According to a particular embodiment, the dye composition as defined previously also comprises one or more additional natural ortho-diphenols as defined previously.

According to another advantageous variant of the invention, the dye composition also comprises iv) hydrogen peroxide or one or more hydrogen peroxide-generating systems as defined previously.

According to another particular variant of the invention, the dye composition also comprises one or more basifying agents as defined previously.

Adjuvants:

The composition(s) of the dyeing process in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

Said adjuvants are preferably chosen from surfactants such as anionic or nonionic surfactants or mixtures thereof and mineral or organic thickeners.

The above adjuvants are generally present in an amount for each of them of between 0.01% and 40% by weight relative to the weight of the composition, and preferably between 0.1% and 20% by weight relative to the weight of the composition.

Needless to say, a person skilled in the art will take care to select this or these optional additional compound(s) such that the advantageous properties intrinsically associated with the composition(s) that are useful in the dyeing process in accordance with the invention are not, or are not substantially, adversely affected by the envisioned addition(s).

Additional Dyes:

The process using compositions (A) as defined previously and (B) as defined below and the ingredients i) to v) as defined previously may also use or comprise one or more additional direct dyes. These direct dyes are chosen, for example, from those conventionally used in direct dyeing, and among which mention may be made of any commonly used aromatic and/or non-aromatic dyes such as neutral, acidic or cationic nitrobenzene direct dyes, neutral, acidic or cationic azo direct dyes, natural direct dyes other than ortho-diphenols, neutral, acidic or cationic quinone and in particular anthraquinone direct dyes, azine, triarylmethane, indoamine, methine, styryl, porphyrin, metalloporphyrin, phthalocyanine and methine cyanine direct dyes, and fluorescent dyes. All these additional dyes are other than the ortho-diphenol derivatives according to the invention.

Mention may be made, among natural direct dyes, of lawsone, juglone, indigo, isatin, curcumin, spinulosin, apigenidin and orceins. Use may also be made of extracts or decoctions comprising these natural dyes and in particular henna-based extracts or poultices.

The additional direct dye(s) used in the composition(s) preferably represent from 0.001% to 10% by weight approximately of the total weight of the composition(s) comprising them and more preferentially still from 0.05% to 5% by weight approximately.

The compositions of the process using ingredients i) to v) as defined previously may also use or comprise one or more oxidation bases and/or one or more couplers conventionally used for the dyeing of keratin fibres other than compounds i) and ii).

Among the oxidation bases, mention may be made of para-phenylenediamines, bis(phenyl)alkylenediamines, para-aminophenols, bis-para-aminophenols, ortho-aminophenols and heterocyclic bases, and the addition salts thereof.

Among these couplers, mention may be made especially of meta-phenylenediamines, meta-aminophenols, meta-diphenols and heterocyclic couplers, and the addition salts thereof.

The oxidation base(s) present in the composition(s) are generally each present in an amount of between 0.001% and 10% by weight relative to the total weight of the corresponding composition(s).

The coupler(s) present in the composition(s) are generally each present in an amount of between 0.001% and 10% by weight relative to the total weight of the corresponding composition(s).

Preferably, the process using compounds i) and ii) and composition (A) do not comprise any additional oxidation dyes chosen from oxidation bases and couplers.

The cosmetic composition(s) of the invention may be in various galenical forms, such as a powder, a lotion, a mousse, a cream or a gel, or in any other form that is suitable for dyeing keratin fibres. They may also be packaged in a propellant-free pump-action bottle or under pressure in an aerosol container in the presence of a propellant and form a mousse.

pH of the Composition(s)

According to a particular embodiment of the invention, the pH of the composition(s) containing the basifying agent(s) is greater than 7 and preferably ranges from 8 to 12. More particularly, it is from 8 to 10.

The pH of the composition containing hydrogen peroxide or a hydrogen peroxide-generating system, i.e. composition (A), is preferably less than 7 and more particularly ranges from 1 to 5.

The pH of these compositions may be adjusted to the desired value by means of acidifying or basifying agents usually used in the dyeing of keratin fibres, chosen especially from the ingredients v) as defined previously, or alternatively using standard buffer systems.

Among the acidifying agents for the compositions used in the invention, examples that may be mentioned include mineral or organic acids, for instance hydrochloric acid, orthophosphoric acid, sulfuric acid, carboxylic acids, for instance acetic acid, tartaric acid, citric acid or lactic acid, or sulfonic acids.

vii) Dyeing Process

The dyeing process of the invention is a process in which keratin fibres, more particularly human keratin fibres such as the hair, are treated with a composition (A) comprising:
  i) one or more indole or indoline compounds as defined previously; and
  ii) one or more aromatic compounds comprising a hydrocarbon-based polycycle comprising at least 10 carbon atoms, at least one of the rings of which is aromatic, as defined previously.

According to an advantageous variant of the invention, the process of the invention uses iii) one or more metal salts as defined previously. Preferentially, composition (A) of the process also comprises iii) one or more metal salts as defined previously.

Preferentially, the process for dyeing keratin fibres of the invention uses iv) hydrogen peroxide or one or more hydrogen peroxide-generating systems. More preferably, the ingredient(s) iv) are in composition (A) as defined previously.

In particular, the dyeing process uses, preferably after applying composition (A), an alkaline composition (B) which comprises v) one or more basifying agents.

The leave-on time after application of compositions (A) and (B) is set at between 3 and 120 minutes, preferentially between 10 and 60 minutes and more preferentially between 15 and 45 minutes.

The keratin fibres may or may not be moistened beforehand.

According to a particular dyeing process of the invention, said process may be followed by post-treatment steps such as shampooing using a standard shampoo, rinsing, for example with water, and/or drying the keratin fibres by heat treatment as defined below.

Preferentially, said process does not involve intermediate rinsing between the applications of compositions (A) and (B) as defined previously.

Preferably, between the application of composition (A) and the application of composition (B) of the dyeing process of the invention, the fibres are:
  a) either wiped mechanically as described below,
  b) or dried by heat with a heat treatment as described below,
  c) or not rinsed, i.e. the application of compositions (A) and (B) as defined previously is performed successively.

According to a particularly preferred process of the invention, just before the step that uses ingredient v), the fibres are a) wiped mechanically.

More preferentially, between the first and second step, the fibres are wiped, preferentially using a towel or absorbent paper, or are dried by heat with a heat treatment at a temperature particularly between 60 and 220° C. and preferably between 120 and 200° C.

Irrespective of the application method, the application temperature is generally between room temperature (15 to 25° C.) and 80° C. and more particularly between 15 and 45° C. Thus, after application of the composition according to the invention, the head of hair may advantageously be subjected to a heat treatment by heating to a temperature of between 30 and 60° C. In practice, this operation may be performed using a styling hood, a hairdryer, an infrared ray dispenser or other standard heating appliances.

Use may be made, both as means for heating and for smoothing the head of hair, of a heating iron at a temperature of between 60° C. and 220° C. and preferably between 120° C. and 200° C.

A particular embodiment of the invention relates to a dyeing process which is performed at room temperature (25° C.).

In all the particular modes and variants of the processes described previously, the mentioned compositions (A) and (B) are ready-to-use compositions that may result from the extemporaneous mixing of two or more compositions and especially of compositions present in dyeing kits. This is especially true for composition (A), which may originate from the mixing of a composition (A1) comprising iv) hydrogen peroxide or one or more hydrogen peroxide-generating systems and of a composition (A2) comprising i) one or more indole or indoline compounds as defined previously, ii) one or more aromatic compounds comprising a hydrocarbon-based polycycle comprising at least 10 carbon atoms, at least one of the rings of which is aromatic, as defined previously, and iii) one or more metal salts.

Composition (A) may also originate from the mixing of a composition (A'1) comprising iv) hydrogen peroxide or one or more hydrogen peroxide-generating systems, of a composition (A'2) comprising i) one or more indole or indoline compounds as defined previously, ii) one or more aromatic compounds comprising a hydrocarbon-based polycycle comprising at least 10 carbon atoms, at least one of the rings of which is aromatic, as defined previously, and optionally of a composition (A'3) comprising iii) one or more metal salts.

viii) Step(s) of Mechanical Wiping and/or Drying:

According to one particular mode of the invention, the process for dyeing keratin fibres comprises at least one intermediate step of mechanical wiping of the fibres and/or of drying and/or leave-in. The steps of intermediate mechanical wiping and drying are also known as "controlled leave-in" to distinguish from "conventional copious rinsing with water" and "leave-in".

The term "mechanical wiping of the fibres" means rubbing an absorbent article on the fibres and physical removal, by means of the absorbent article, of the excess ingredient(s) that have not penetrated the fibres. The absorbent article may be a piece of fabric such as a towel, particularly a terry towel, a cloth or absorbent paper such as household roll towel.

According to a particularly advantageous process of the invention, the mechanical wiping is performed without total drying of the fibre, leaving the fibre moist.

The term "drying" means the action of evaporating the organic solvents and/or water that are in one or more compositions used in the process of the invention, comprising or not comprising one or more ingredients i) to v) as defined previously. The drying may be performed with a source of heat (convection, conduction or radiation) by sending, for example, a stream of hot gas such as air necessary to evaporate the solvent(s). Sources of heat that may be mentioned include a hairdryer, a hairstyling hood, a hair-straightening iron, an infrared ray dispenser or other standard heating appliances.

ix) Dyeing Device or "Kit":

Another subject of the invention is a multi-compartment device for dyeing keratin fibres or "kit" for dyeing keratin fibres. Advantageously, this kit comprises from 2 to 5 compartments containing from 2 to 5 compositions in which are distributed i) one or more indole or indoline compounds as defined previously, ii) one or more aromatic compounds comprising a hydrocarbon-based polycycle comprising at least 10 carbon atoms, at least one of the rings of which is aromatic as defined previously, optionally iii) one or more metal salts as defined previously, optionally iv) hydrogen peroxide or one or more hydrogen peroxide-generating systems as defined previously, and optionally v) one or more basifying agents as defined previously.

According to a first variant, the kit comprises at least four compartments, the first compartment comprising a composition containing iii) as defined previously; the second compartment comprising a composition containing iv) as defined previously; the third compartment containing a composition (B) containing v) as defined previously;
  either the fourth compartment comprises a cosmetic composition containing i) as defined previously; and ii) as defined previously;
  or the fourth compartment comprises i) as defined previously, in which case a fifth compartment comprises ii) as defined previously.

In this other embodiment, at least one of the three compositions is preferably aqueous and i) and/or ii) as defined previously may be in powder form.

A three-compartment kit may also be provided, the first compartment a) containing a composition comprising i) as defined previously, ii) as defined previously; and iii) as defined previously; the second b) containing a composition comprising iv) as defined previously; and the third c)

containing a composition comprising v) as defined previously. In this other kit, at least one of the compositions is preferably aqueous. This composition preferably contains hydrogen peroxide.

According to a particular embodiment of the invention, the kit contains three compartments and comprises: a first compartment comprising a composition containing i) as defined previously, ii) as defined previously; the second compartment comprising iii) as defined previously, iv) as defined previously; and a third compartment containing v) as defined previously.

Among the two-compartment kits, the following kits are preferred:
  kit 1 in which the first composition contained in the first compartment contains: i), ii), iii) and iv) as defined previously; and then in the second compartment v) as defined previously;
  kit 2 in which the first compartment contains: i), ii), and v) as defined previously; and then in the second compartment iii) and iv) as defined previously.

According to one variant, the device according to the invention also comprises an additional composition (C) comprising one or more treating agents.

The compositions of the device according to the invention are packaged in separate compartments, optionally accompanied by suitable application means which may be identical or different, such as fine brushes, coarse brushes or sponges.

The device mentioned above may also be equipped with a means for dispensing the desired mixture on the hair, for instance the devices described in patent FR 2 586 913.

DYEING EXAMPLES

Compositions A1, A2 and B were prepared as follows:
The values given in Tables 1 and 2 are given in g per 100 g of composition:

TABLE 1

| Ingredients | A1 Comparative | A2 Invention |
|---|---|---|
| 5,6-Dihydroxyindole, i) | 0.5 | 0.5 |
| 2,7-Dihydroxynaphthalene, ii) | — | 1 |
| Manganese gluconate iii) | 0.2 | 0.2 |
| Hydrogen peroxide, iv) | 2.4 | 2.4 |
| Propanediol | 5 | 5 |
| Caprylyl/capryl glucoside | 2 | 2 |
| Denatured alcohol | 5 | 5 |
| Demineralized water | qs 100 g | qs 100 g |

TABLE 2

| Ingredients | B |
|---|---|
| Sodium bicarbonate | 5 |
| Monoethanolamine (MEA) | 2 |
| Hydroxyethylcellulose (HEC) | 1.5 |
| Demineralized water | qs 100 g |

For the 3 Tests:
  Each composition A1 and A2 is applied to locks of natural Caucasian hair containing 90% white hairs. The compositions are then left on the locks for 30 minutes at 27° C.
  After this leave-on time, the hair impregnated with the first composition is wiped using an absorbent paper towel. Immediately after wiping, without waiting for the hair to dry, composition B is applied; the leave-on time is 2 minutes at room temperature.

Next, the lock is rinsed with tap water, shampooed with a standard shampoo (Ultra doux camomile), rinsed with tap water and dried under a hood at 40° C.

Composition A2 according to the invention gives a more powerful colouring than composition A1.

Colorimetric Results:

The hair colouring is measured using a Minolta spectrocolorimeter (CM2600d, illuminant D65, angle 10°, specular component included) in the CIELab system.

In this L* a* b* system, L* represents the intensity of the colour, a* indicates the green/red colour axis and b* indicates the blue/yellow colour axis. The lower the value of L, the darker or more intense the colour. The higher the value of a*, the redder the shade and, the higher the value of b*, the yellower the shade.

The chromaticity C* is calculated using the equation:

$$C^* = \sqrt{a^{*2} + b^{*2}}$$

The colorimetric measurements were taken before exposure to light, and then after exposure to light.

The locks dyed using the compositions described above were exposed to light according to the following protocol:

The dyed locks are exposed to light using a Xenotest 150S machine from the company Atlas at an average lighting level (about 1250 W/m² between 300 and 800 nm for 7 infrared filters). The humidity level is set at 60%. The exposure time is 40 hours.

In this L*, a*, b* system, L* represents the intensity of the color, a* indicates the green/red color axis and b* indicates the blue/yellow color axis. The lower the value of L, the darker or more intense the color. The higher the value of a*, the redder the shade; the higher the value of b*, the yellower the shade.

The variation in coloring between the colored locks which is not exposure to light (control) and after coloration and exposure to light are defined by ΔE*, corresponding to the colour fastness to light on keratin fibers, according to the following equation:

$$\Delta E = \sqrt{(L^* - L_o^*)^2 + (a^* - a_o^*)^2 + (b^* - b_o^*)^2}$$

In this equation, L*, a* and b* represent the values measured after the exposure to light of the colored hair and $L_o^*$, $a_o^*$ and $b_o^*$ represent the values measured before the exposure to light of the colored hair.

The more important ΔE is, the higher difference of the color before and after the light exposure of the hair, which corresponds to weaker light fastness.

Results on ΔE and ΔC:

TABLE 3

| | before Xenotest | | |
|---|---|---|---|
| | Lock before dyeing | A1 + B (Comparative) | A2 + B (Invention) |
| L* | 66.4 | 24.8 | 21.6 |
| a* | 0.8 | 0.1 | 0.3 |
| b* | 16.5 | 0.5 | 0.3 |
| ΔE | — | 44.6 | 47.6 |

TABLE 4

After Xenotest

| | Lock before dyeing | A1 + B (Comparative) | A2 + B (Invention) |
|---|---|---|---|
| L* | 66.4 | 24.5 | 20.1 |
| a* | 0.8 | 0.9 | 0.6 |
| b* | 16.5 | 3.7 | 1.2 |
| ΔE | — | 43.8 | 48.8 |

TABLE 5

Results Δb after-before Xenotest

| | A1 + B (Comparative) | A2 + B (Invention) |
|---|---|---|
| difference Δb after-before exposure | 3.2 | 0.9 |

According to the results of the tables 3 and 4 it appears that composition of the invention allows to obtain a significantly higher color uptake than the comparative one. Moreover, according to the table 5, the Δb value after and before the xenotest treatment is significant for the dyeing process A1+B (comparative) than the dyeing process A2+B (invention).

Chromaticity:

The change of colour after exposure to light is reflected by the variation in the chromaticity ΔC, and in particular the change towards yellow by the variation in b*Δb on the blue/yellow colour axis
with $\Delta C = C^* - C_0^*$, $C^*$ corresponding to the chromaticity after exposure to light and $C_0^*$ to the chromaticity before exposure to light,
and $\Delta b = b^* - b_0^*$, $b^*$ corresponding to the value after exposure to light and $b_0^*$ to the value before exposure to light.

TABLE 6

| Dyeing process | Xenotest | a* | b* | C* | ΔC |
|---|---|---|---|---|---|
| A2 + B (invention) | Before exposure | 0.3 | 0.3 | 0.4 | 0.9 |
| | After exposure | 0.6 | 1.2 | 1.3 | |
| A1 + B (comparative) | Before exposure | 0.1 | 0.5 | 0.5 | 3.3 |
| | After exposure | 0.9 | 3.7 | 3.8 | |

The values of ΔC and Δb are lower in the case of composition A2 than composition A1: composition A2 leads to less changing of the colour, in particular towards yellow, than composition A1.

Compositions A3 to A5:

The values given in Table 7 are given in g per 100 g of composition:

TABLE 7

| Ingredients | A3 Invention | A4 Invention | A5 Invention |
|---|---|---|---|
| 5,6-Dihydroxyindole, i) | 0.5 | 0.5 | 0.5 |
| 1,5-Dihydroxynaphthalene, iii) | 1 | — | — |
| 1-Hydroxy-naphthalene, iv) | — | 1 | — |
| 2-Methyl-1-naphthol, vi) | — | — | 1 |
| Manganese gluconate vii) | 0.2 | 0.2 | 0.2 |
| Hydrogen peroxide, viii) | 2.4 | 2.4 | 2.4 |
| Propanediol, | 5 | 5 | 5 |
| Caprylyl/capryl glucoside | 2 | 2 | 2 |
| Denatured alcohol | 5 | 5 | 5 |
| Demineralized water | qs 100 g | qs 100 g | qs 100 g |

Each composition A3 to A5 is applied to locks of natural Caucasian hair containing 90% white hairs. The compositions are then left on the locks for 30 minutes at 27° C.

After this leave-on time, the hair impregnated with the first composition is wiped using an absorbent paper towel. Immediately after wiping, without waiting for the hair to dry, composition B is applied; the leave-on time is 2 minutes at room temperature.

Next, the lock is rinsed with tap water, shampooed with a standard shampoo (Ultra doux camomile), rinsed with tap water and dried under a hood at 40° C.

It has been observed that composition according to the invention containing i) 5,6-dihydroxyindole with ii) 2,7-naphtalendiol, 1,5-naphtalendiol, 1-hydroxynaphtol and 2-methy-1-naphtol and iii) metal salt in particular manganese salt allow to obtain a high level of colour uptake DE and/or intensive colour. The fastness of the colour especially vs the light is also good. On the other hand it has been observed that 2,7-naphtalendiol, 1,5-naphtalendiol, 1-hydroxynaphtol and 2-methy-1-naphtol allow to avoid the changing of the colour, in particular towards yellow.

The invention claimed is:

1. A process for dyeing keratin fibers, comprising applying to the fibers a composition (A) comprising:
   i) at least one indole or indoline compound;
   ii) at least one aromatic compound comprising a hydrocarbon-based polycycle comprising at least 10 carbon atoms, wherein at least one ring is aromatic and substituted with at least one hydroxyl or amino group; and
   iii) at least one metal salt chosen from transition metal salts, rare-earth metal salts, or mixtures thereof.

2. The process according to claim 1, wherein the at least one indole or indoline compound is chosen from compounds of formula (I) below:

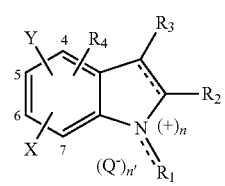

(I)

or organic or mineral acid or base salts thereof, optical isomers thereof, enantiomers or diastereoisomers, geometrical isomers or tautomers thereof, oligomers thereof, or solvates thereof, wherein:

$R_1$ is chosen from a hydrogen atom, $(C_1-C_6)$alkyl, $(C_2-C_6)$alkenyl, $(C_1-C_6)$alkylcarbonyl, $(C_2-C_6)$alkenylcarbonyl, $(C_1-C_6)$alkylthiocarbonyl, $(C_2-C_6)$alkenylthiocarbonyl radical, or a radical $R_g$—O—S(O)$_x$—, wherein $R_g$ is a hydrogen atom, an alkali metal or alkaline-earth metal, or a $(C_1-C_4)$alkyl and x is equal to 1 or 2, said alkyl or alkenyl groups being optionally substituted;

$R_2$ is chosen from a hydrogen atom, $(C_1-C_6)$alkyl radical, or —C(Z)—Z'—$R_a$; wherein $R_a$ is chosen from a hydrogen atom, an alkali metal or alkaline-earth metal, or a $(C_1-C_6)$alkyl radical; Z and Z' are independently chosen from an oxygen or sulfur atom, a group $NR_b$, or $N^+R_bR_c$, $Q'^-$; Z' may also be chosen from a covalent a bond with $R_b$ and $R_c$, which may be identical or different, representing a hydrogen atom or a $(C_1-C_6)$ alkyl radical and $Q'^-$ is an anionic counterion;

$R_3$ is chosen from:
i) a hydrogen atom;
ii) a $(C_1-C_6)$alkyl radical optionally substituted especially with a group $-NR_bR_c$, $-N^+R_aR_bR_c$, $Q'^-$ or $-C(Z)-Z'-R_a$, wherein $R_a$ is chosen from a hydrogen atom, an alkali metal or alkaline-earth metal, or a $(C_1-C_6)$alkyl radical; Z and Z' are independently chosen from an oxygen or sulfur atom, a group $NR_b$, or $N^+R_bR_c$, $Q'^-$; Z' may also be chosen from a covalent a bond with $R_b$ and $R_c$, which may be identical or different, representing a hydrogen atom or a $(C_1-C_6)$alkyl radical and $Q'^-$ represents an anionic counterion;
iii) a radical corresponding to formula (II) below:

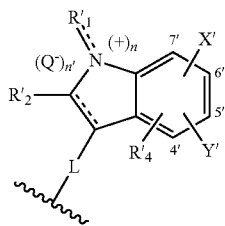

(II)

wherein:
L is chosen from a covalent a bond, or a divalent group chosen from $-Z-$, $-C(Z)-Z'-$, or a divalent group $(C_1-C_6)$alkylene wherein Z and Z' as defined previously;
$R'_1$, $R'_2$ and $R'_4$ represent the same atoms or radicals as $R_1$, $R_2$ and $R_4$, respectively;

∿∿∿ is the point of attachment of the radical (II) to the rest of the molecule;
or alternatively $R_1$ and $R_2$ and/or $R_2$ and $R_3$ form, together with the atoms that bear them, a fused, optionally substituted heterocyclic group; or $R_2$ and $R_3$ form, together with the carbon atoms that bear them, a fused, optionally substituted aryl group;

$R_4$ is chosen from:
i) a hydrogen atom;
ii) a halogen atom;
iii) a group $-NRR'$;
iv) an $-OH$ group;
v) a $(C_1-C_6)$alkyl radical;
vi) a $(C_1-C_6)$alkoxy radical;
vii) a $(C_1-C_6)$alkylthio radical;
viii) an aryloxy radical;
ix) an arylthio radical;
x) an aryl$(C_1-C_6)$alkoxy radical;
xi) an aryl$(C_1-C_6)$alkylthio radical;
xii) a radical $R_aC(Z_a)-Z_b-$ wherein $Z_a$ and $Z_b$ is chosen from an oxygen or sulfur atom or $NR_b$, $R_a$ and $R_b$ are as defined previously, or xiii) a radical corresponding to formula (III) below:

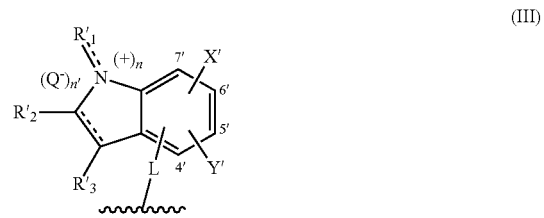

(III)

wherein:
L is as defined previously,
$R'_1$, $R'_2$ and $R'_3$ represent the same atoms or radicals as $R_1$, $R_2$ and $R_3$, respectively;

∿∿∿ represents the point of attachment of the radical (III) to the rest of the molecule;
X and X', which may be identical or different, is a hydrogen atom or a $-NRR'$ radical chosen from $-NH_2$, $-OR_e$, $-SR_e$, $(C_1-C_6)$alkyl, or $R_a-C(Z_a)-Z_b-$ as defined previously, where $R_e$ is chosen from a hydrogen atom, a group $(C_1-C_6)$alkyl, aryl, or aryl$(C_1-C_6)$alkyl;
Y and Y', which may be identical or different, are chosen from $-OR'_e$, $-SR'_e$, $-NRR'$, $R_f-O-S(O)_x-Z_d-$ or $R_f-O-S(O)_x-$ wherein $R_f$ is chosen from a hydrogen atom, an alkali metal or alkaline-earth metal, or a $(C_1-C_4)$alkyl, $Z_d$ is chosen from an oxygen atom or a group NR with R as defined previously, x as defined previously and $R'_e$ representing the same atoms or radicals as $R_e$; or the radicals $R_e$ and $R_e'$ of two contiguous groups X and X' and/or contiguous groups Y and Y' form, together with the oxygen or sulfur atom, a heterocyclic group;
the radicals X, Y, X' and Y' being located on any of the carbon atoms 4 to 7 and 4' to 7', respectively; particularly;
R and R', which may be identical or different, are chosen from a hydrogen atom or an optionally substituted $(C_1-C_6)$alkyl group;

- - - - - represents a single bond or a double bond;
wherein n is 0 when the bond between $R_1$ and N or $R'_1$ and N is a single bond; or n is 1 when $R_1$ or $R'_1$ is an alkenyl group and when the end linked to the nitrogen atom is a double bond;
$Q^-$ is an anionic counterion;
n' is 0 or 1;
wherein:
$R_3$ cannot represent the radical (II) when $R_4$ represents the radical (III); and
when n is 0, then n' is 0; when n is 1, then n' is 1; or when n' is 0, a radical $-C(Z)Z'-R_a$ is in the anionic form $-C(Z)-Z'^-$.

3. The process according to claim 2, wherein the compounds of formula (I) are monomers and $R_3$ is chosen from a hydrogen atom or an optionally substituted $(C_1-C_6)$alkyl radical.

4. The process according to claim 2, wherein the compounds of formula (I) are indole compounds wherein the

----- bond between the carbon atoms bearing the radicals $R_2$ and $R_3$ is a double bond.

5. The process according to claim 2, wherein the compounds of formula (I) are chosen from the indole compounds of formula (Ia) below, or the organic or mineral acid or base salts thereof:

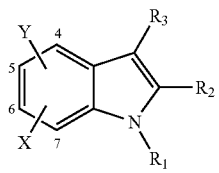

(Ia)

wherein:
  $R_1$ and $R_3$, which may be identical or different, are chosen from a hydrogen atom or a $C_1$-$C_4$ alkyl radical;
  $R_2$ is chosen from a hydrogen atom or a $C_1$-$C_4$ or —C(O)—OH radical;
  X is chosen from a hydrogen atom, —$NH_2$, —OH, a $C_1$-$C_4$ alkyl radical, a $C_1$-$C_4$ alkoxy radical, or a radical —O—C(O)—R wherein R is chosen from H or $C_1$-$C_4$ alkyl;
  Y is chosen from —OH, —$NH_2$, or a radical —O—C(O)R wherein R is chosen from H or $C_1$-$C_4$ alkyl,
or the organic or mineral acid or base salts thereof.

6. The process according to claim 5, wherein the indole compounds of formula (Ia) are chosen from 5,6-dihydroxyindole, 2-methyl-5,6-dihydroxyindole, 3-methyl-5,6-dihydroxyindole, 4-hydroxyindole, 2,3-dimethyl-5,6-dihydroxyindole, 6-hydroxy 5-methoxyindole, 6-hydroxyindole, 5-hydroxyindole, 7-hydroxyindole, 7-aminoindole, 5-aminoindole, 5,6-dihydroxyindole-2-carboxylic acid, 5-aminoindole, 1-methyl-5,6-dihydroxyindole, 5-acetyloxy-6-hydroxyindole, 6-acetyl-5-hydroxyindole and 5,6-diacetyloxyindole, or the organic or mineral acid or base salts thereof.

7. The process according to claim 1, wherein the at least one indole compound is chosen from:

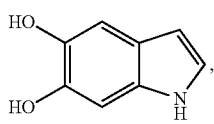

(1)

5,6-dihydroxyindole

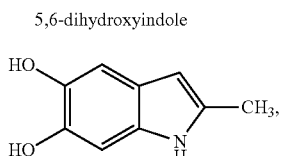

(2)

2-methyl-5,6-dihydroxyindole

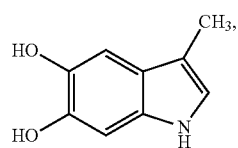

(3)

3-methyl-5,6-dihydroxyindole

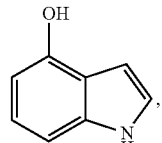

(4)

4-dihydroxyindole

(5)

2,3-dimethyl-5,6-dihydroxyindole

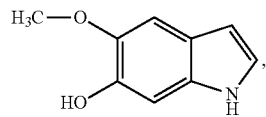

(6)

6-hydroxy-5-methoxyindole

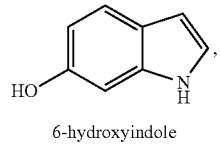

(7)

6-hydroxyindole

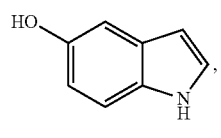

(8)

5-hydroxyindole

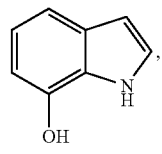

(9)

7-hydroxyindole

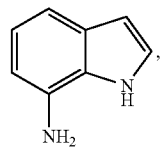

(10)

7-aminoindole

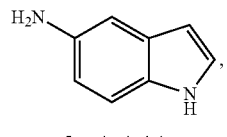

(11)

5-aminoindole

-continued

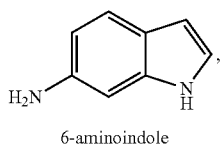
6-aminoindole

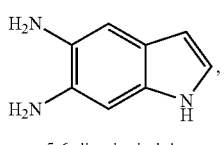
5,6-diaminoindole

4-aminoindole

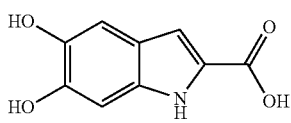
5,6-dihydroxyindole-2-carboxylic acid, or
5,6-dihydroxy-1H-indole-2-carboxylic acid

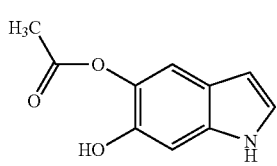
5-acetyloxy-6-hydroxyindole

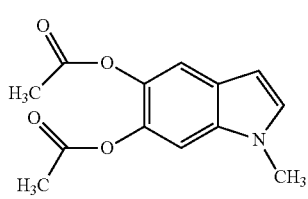
5,6-dimethylcarbonyloxy-1-methyl-1H-indole

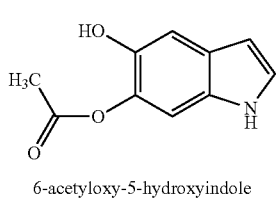
6-acetyloxy-5-hydroxyindole

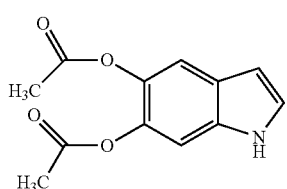
5,6-diacetyloxyindole

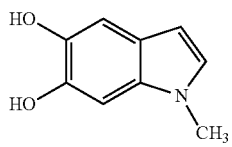
5,6-dihydroxy-1-methyl-1H-indole or 1-methyl-5,6-dihydroxyindole

6-hydroxy-5-methoxyindole

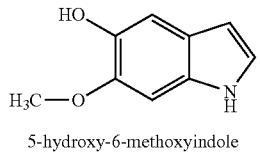
5-hydroxy-6-methoxyindole

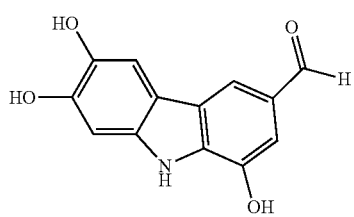
1,6,7-trihydroxy-9H-carbazole-3-carboxaldehyde

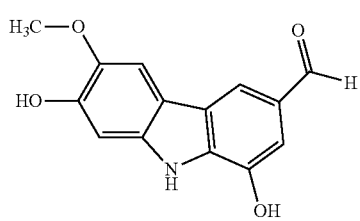
1,7-dihydroxy-6-methoxy-9H-carbazole-3-carboxaldehyde

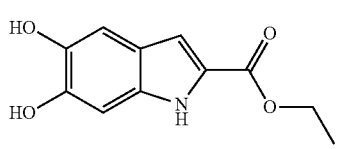
ethyl 5,6-dihydroxy-1H-indole-2-carboxylate

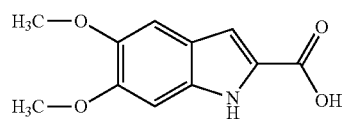
5,6-dimethoxy-1H-indole-2-carboxylate acid

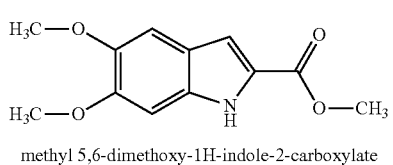
methyl 5,6-dimethoxy-1H-indole-2-carboxylate

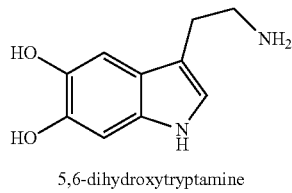
5,6-dihydroxytryptamine
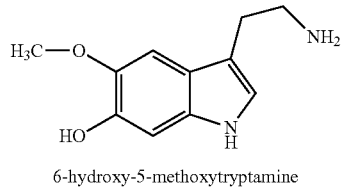
6-hydroxy-5-methoxytryptamine
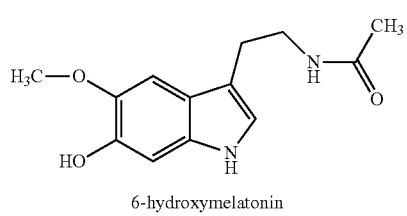
6-hydroxymelatonin
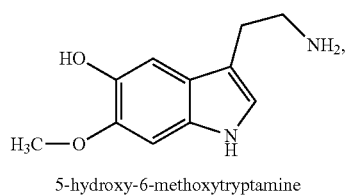
5-hydroxy-6-methoxytryptamine
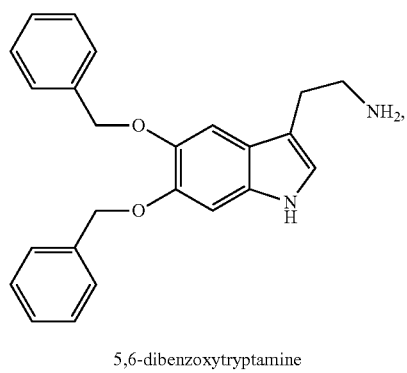
5,6-dibenzoxytryptamine
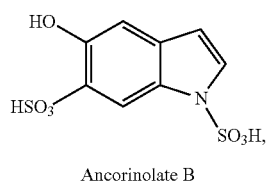
Ancorinolate B
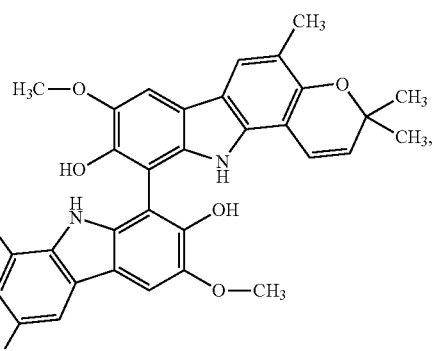
8,8′-bikoenigine
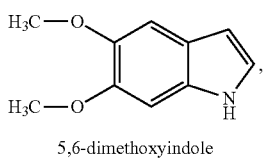
5,6-dimethoxyindole
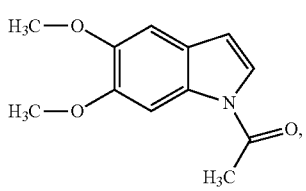
5,6-dimethoxy-1-acetyl-1H-indole
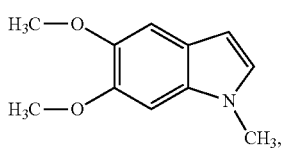
5,6-dimethoxy-1-methyl-1H-indole
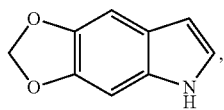
5,6-methylenedioxyindole
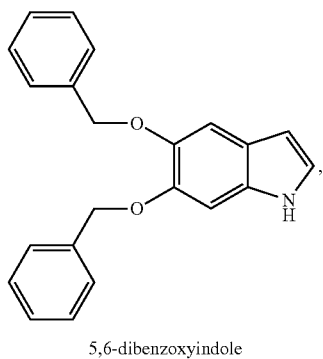
5,6-dibenzoxyindole (40)

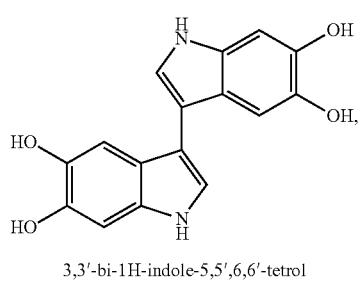

3,3'-bi-1H-indole-5,5',6,6'-tetrol (41)

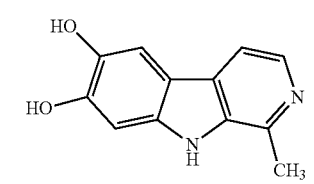

6,7-dihydroxy-1-methyl-β-carboline or 1-methyl-9H-pyrido[3,4-b]indole-6,7-diol (42)

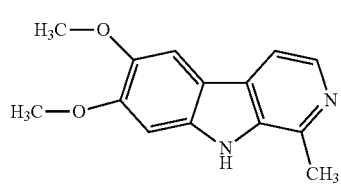

6,7-dimethoxy-1-methyl-β-carboline or 1-methyl-9H-pyrido[3,4-b]indole-6,7-diol (43)

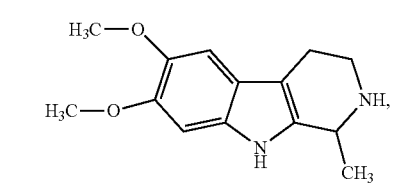

1,2,3,4-tetrahydro-6,7-dimethoxy-1-methyl-β-carboline (44)

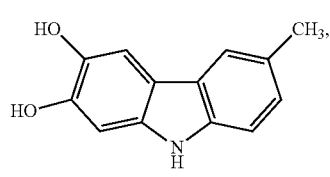

2,3,-dihydroxy-6-methyl-9H-carbazole (45)

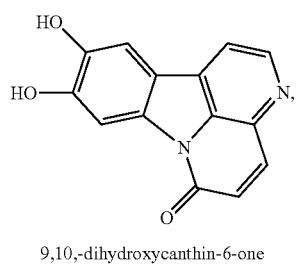

9,10,-dihydroxycanthin-6-one (46)

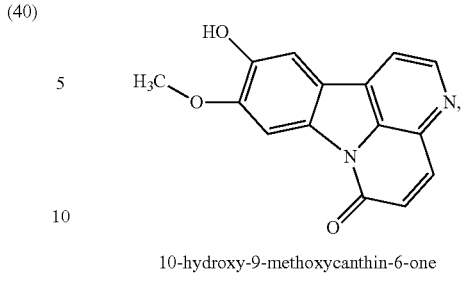

10-hydroxy-9-methoxycanthin-6-one (47)

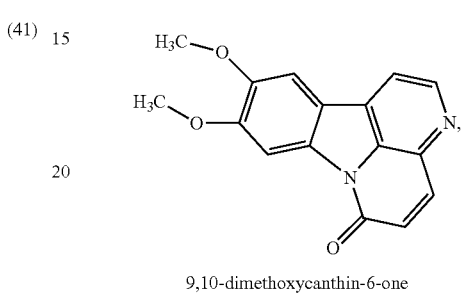

9,10-dimethoxycanthin-6-one (48)

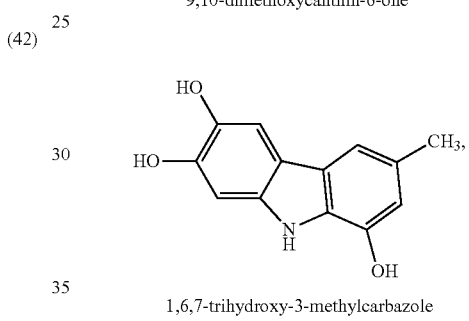

1,6,7-trihydroxy-3-methylcarbazole (49)

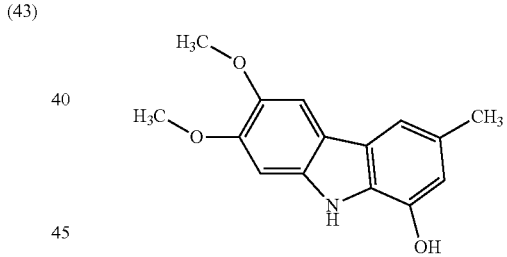

1-hydroxy-6,7-dimethoxy-3-methylcarbazole (50)

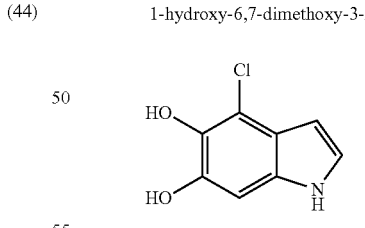

4-chloro-5,6-dihydroxyindole (51)

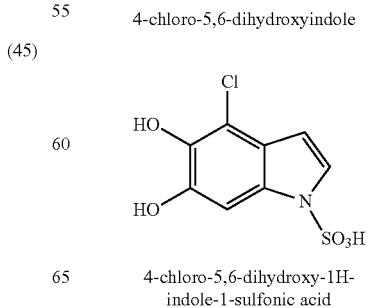

4-chloro-5,6-dihydroxy-1H-indole-1-sulfonic acid (52)

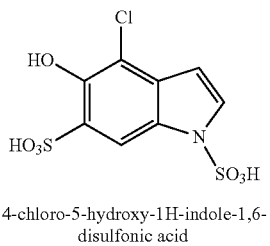

4-chloro-5-hydroxy-1H-indole-1,6-disulfonic acid or the organic or mineral acid or base salts thereof.

8. The process according to claim 2, wherein the compounds of formula (I) are chosen from the indoline compounds of formula (Ib) below, or the enantiomers and diastereoisomers thereof or the organic or mineral acid or base salts thereof:

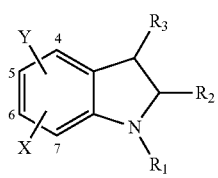

(Ib)

wherein:
$R_1$ and $R_3$, which may be identical or different, are chosen from a hydrogen atom or a $C_1$-$C_4$ alkyl radical;
$R_2$ is chosen from a hydrogen atom or a $C_1$-$C_4$ or —C(O)—OH radical;
X is chosen from a hydrogen atom, —NH$_2$, —OH, a $C_1$-$C_4$ alkyl radical, a $C_1$-$C_4$ alkoxy radical, or a radical —O—C(O)—R wherein R is chosen from H or $C_1$-$C_4$ alkyl;
Y is chosen from —OH, —NH$_2$ or a radical —O—C(O)R wherein R is chosen from H or $C_1$-$C_4$ alkyl,
or the organic or mineral acid or base salts thereof.

9. The process according to claim 1, wherein composition (A) comprises at least one indole or indoline compound chosen from 5,6-dihydroxyindole or 5,6-dihydroxyindoline.

10. The process according to claim 1, wherein composition (A) comprises at least one aromatic compound comprising a hydrocarbon-based polycycle comprising at least 10 carbon atoms, wherein at least one of the rings of which is aromatic, chosen from compounds corresponding to formula (II) below:

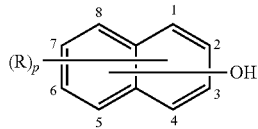

(II)

or the organic or mineral acid or base salts thereof, optical isomers thereof, enantiomers or diastereoisomers, geometrical isomers or tautomers thereof, or solvates thereof;
wherein:
R, which may be identical or different, is chosen from a halogen atom, a ($C_1$-$C_6$)alkyl group, ($C_1$-$C_6$)alkoxy group, ($C_1$-$C_6$)alkylthio, (di)($C_1$-$C_6$)(alkyl)amino group, hydroxyl group, thio, heterocyclic group, pyperidinyl group, or ($C_1$-$C_6$)(alkyl)piperazinyl group; and
p is an integer chosen from 0, 1, 2, 3, 4, 5, 6 or 7.

11. The process according to claim 1, wherein composition (A) comprises at least one aromatic compound comprising a hydrocarbon-based polycycle comprising at least 10 carbon atoms, wherein at least one ring is aromatic chosen from 2,7-Naphthalenediol; 1,5-Naphthalenediol; 1-Hydroxy-naphthalene; and 2-Methyl-1-naphthol.

12. The process according to claim 1, wherein composition (A) comprises at least one metal salt chosen from iron, manganese, or zinc salts.

13. The process according to claim 1, wherein composition (A) comprises at least one metal salt chosen from metal salts in oxidation state II that bear two ligands derived from (poly)hydroxy acid.

14. The process according to claim 1, wherein composition (A) comprises at least one metal salt chosen from salts complexed with two carboxylate groups chosen from compounds of formula (VI) below:

R—C(O)—O-M-O—C(O)—R' (VI)

and the solvates or enantiomers thereof, wherein:
M is chosen from a metal (II) or metal$^{2+}$ in oxidation state 2; and
R and R', which may be identical or different, are a ($C_1$-$C_6$)(poly)hydroxyalkyl group.

15. The process according to claim 1, wherein the at least one metal salt is chosen from organic acid salts chosen from citrates, lactates, glycolates, gluconates, acetates, propionates, fumarates, oxalates, or tartrates.

16. The process according to claim 1, further comprising at least one natural ortho-diphenol other than the indole or indoline compounds, wherein the at least one natural ortho-diphenol is chosen from extracts of tea or rose leaves, extracts of rosemary leaves, extracts of mate leaves, extracts of fruit, extracts of legumes, extracts of tree wood, extracts of quebracho wood, extracts of braziletto wood, or extracts of gall nuts.

17. The process according to claim 1, further comprising hydrogen peroxide or at least one hydrogen peroxide-generating system.

18. The process according to claim 1, further comprising a composition (B), composition (B) comprising at least one mineral basifying agent.

19. The process according to claim 18, wherein the at least one mineral basifying agent is chosen from organic amines.

20. The process according to claim 18, wherein the at least one mineral basifying agent is chosen from alkanolamines, diethanolamines, triethanolamines, 2-amino-2-methyl-1-propanol, amino acids, or mixtures thereof.

21. The process according to claim 18, wherein composition (B) is applied to the hair after composition (A).

22. The process according to claim 21, wherein between the application of composition (A) and the application of composition (B), the hair fibers are a) wiped mechanically, b) dried by heat with a heat treatment, or c) not rinsed.

23. A dyeing composition comprising
i) at least one indole or indoline compound;
ii) at least one aromatic compound comprising a hydrocarbon-based polycycle comprising at least 10 carbon atoms, wherein at least one ring is aromatic and substituted with at least one hydroxyl or amino group;
optionally, iii) at least one metal salt chosen from transition metal salts, rare-earth metal salts, or mixtures thereof, or at least one natural ortho-diphenol;

optionally iv) hydrogen peroxide or at least one hydrogen peroxide generating system; and optionally v) at least one basifying agent.

24. A kit for dyeing keratin fibers, comprising at least 2 compartments and at least 2 compositions, the compositions comprising:
- i) at least one indole or indoline compound;
- ii) at least one aromatic compound comprising a hydrocarbon-based polycycle comprising at least 10 carbon atoms, wherein at least one ring is aromatic and substituted with at least one hydroxyl or amino group;
- optionally iii) at least one metal salt;
- optionally iv) hydrogen peroxide or at least one hydrogen peroxide-generating system; and
- optionally v) at least one basifying agent.

* * * * *

UNITED STATES PATENT AND TRADEMARK OFFICE
CERTIFICATE OF CORRECTION

PATENT NO. : 10,292,921 B2
APPLICATION NO. : 15/313716
DATED : May 21, 2019
INVENTOR(S) : Fabien Aubert et al.

It is certified that error appears in the above-identified patent and that said Letters Patent is hereby corrected as shown below:

In the Claims

Column 35, Line 2, after "covalent", please change "a" to -- σ --; (Second Occurrence)

Column 35, Line 14, after "covalent", please change "a" to -- σ --; (Second Occurrence)

Column 35, Line 33, after "covalent", please change "a" to -- σ --; (Second Occurrence)

Column 38, compound (4), please change "4-dihydroxyindole" to -- 4-hydroxyindole --;

Column 40, compound (26), please change "carboxylate" to -- carboxylic --;

Column 43, compound (42), please change "7-diol" to -- 7-dimethoxy --; and

Column 46, Line 37, please change "mate" to -- maté --.

Signed and Sealed this
Twenty-seventh Day of August, 2019

Andrei Iancu
*Director of the United States Patent and Trademark Office*